US012201444B2

United States Patent
Sverdlik et al.

(10) Patent No.: US 12,201,444 B2
(45) Date of Patent: Jan. 21, 2025

(54) METHOD AND/OR APPARATUS FOR MEASURING RENAL DENERVATION EFFECTIVENESS

(71) Applicant: Sonivie Ltd., Rosh HaAyin (IL)

(72) Inventors: Ariel Sverdlik, Tel-Aviv (IL); Benny Dilmoney, Givat Shmuel (IL); Yehuda Zadok, Holon (IL); Or Shabtay, Kibbutz Farod (IL)

(73) Assignee: Sonivie Ltd., Rosh HaAyin (IL)

( * ) Notice: Subject to any disclaimer, the term of this patent is extended or adjusted under 35 U.S.C. 154(b) by 0 days.

(21) Appl. No.: 17/752,879

(22) Filed: May 25, 2022

(65) Prior Publication Data

US 2022/0287634 A1 Sep. 15, 2022

Related U.S. Application Data

(62) Division of application No. 13/905,224, filed on May 30, 2013, now Pat. No. 11,357,447.
(Continued)

(51) Int. Cl.
*A61B 5/00* (2006.01)
*A61B 5/02* (2006.01)
(Continued)

(52) U.S. Cl.
CPC .......... *A61B 5/4848* (2013.01); *A61B 5/0036* (2018.08); *A61B 5/02007* (2013.01);
(Continued)

(58) Field of Classification Search
CPC ....... A61B 5/4848; A61B 5/369; A61B 5/242; A61B 5/02007; A61B 5/0205;
(Continued)

(56) References Cited

U.S. PATENT DOCUMENTS

| 4,319,580 A | 3/1982 | Colley et al. |
| 5,038,789 A | 8/1991 | Frazin |

(Continued)

FOREIGN PATENT DOCUMENTS

| CA | 2954897 | 11/2016 |
| CN | 1279595 | 1/2001 |

(Continued)

OTHER PUBLICATIONS

Communication Pursuant to Article 94(3) EPC Dated Mar. 1, 2023 From the European Patent Office Re. Application No. 18771348.2 (6 Pages).
(Continued)

*Primary Examiner* — Baisakhi Roy

(57) ABSTRACT

The present invention, in some embodiments thereof, relates to methods and/or apparatus for measuring the effectiveness of a renal denervation treatment. In some embodiments, a method for determining effectiveness of the denervation treatment comprises tracking at least one of arterial wall movement, arterial blood flow rate, arterial blood flow velocity, blood pressure and arterial diameter at one or more selected locations in the renal artery over time, and assessing the effectiveness of said renal denervation treatment according to results obtained by tracking.

24 Claims, 9 Drawing Sheets

Related U.S. Application Data

(60) Provisional application No. 61/653,515, filed on May 31, 2012.

(51) Int. Cl.
| | | |
|---|---|---|
| *A61B 5/0205* | (2006.01) | |
| *A61B 5/026* | (2006.01) | |
| *A61B 5/107* | (2006.01) | |
| *A61B 5/242* | (2021.01) | |
| *A61B 5/369* | (2021.01) | |
| *A61B 8/04* | (2006.01) | |
| *A61B 8/06* | (2006.01) | |
| *A61B 8/08* | (2006.01) | |
| *A61B 8/12* | (2006.01) | |
| *A61N 7/02* | (2006.01) | |
| *A61N 7/00* | (2006.01) | |

(52) U.S. Cl.
CPC ............ *A61B 5/0205* (2013.01); *A61B 5/026* (2013.01); *A61B 5/1076* (2013.01); *A61B 5/242* (2021.01); *A61B 5/369* (2021.01); *A61B 8/04* (2013.01); *A61B 8/06* (2013.01); *A61B 8/0891* (2013.01); *A61B 8/12* (2013.01); *A61B 8/485* (2013.01); *A61N 7/022* (2013.01); *A61N 2007/003* (2013.01); *A61N 2007/0052* (2013.01)

(58) Field of Classification Search
CPC ......... A61B 5/026; A61B 5/1076; A61B 8/04; A61B 8/06; A61B 8/12; A61N 7/022
See application file for complete search history.

(56) References Cited

U.S. PATENT DOCUMENTS

| | | |
|---|---|---|
| 5,226,847 A | 7/1993 | Thomas, III et al. |
| 5,421,338 A | 6/1995 | Crowley et al. |
| 5,467,251 A | 11/1995 | Katchmar |
| 5,471,988 A | 12/1995 | Fujio et al. |
| 5,524,630 A | 6/1996 | Crowley |
| 5,590,653 A | 1/1997 | Aida et al. |
| 5,620,417 A | 4/1997 | Jang et al. |
| 5,620,479 A | 4/1997 | Diederich |
| 5,657,760 A | 8/1997 | Ying et al. |
| 5,699,804 A | 12/1997 | Rattner |
| 5,707,367 A | 1/1998 | Nilsson |
| 5,735,280 A | 4/1998 | Sherman et al. |
| 5,762,066 A | 6/1998 | Law et al. |
| 5,772,642 A | 6/1998 | Ciamacco, Jr. et al. |
| 5,895,355 A | 4/1999 | Schaer |
| 5,895,356 A | 4/1999 | Andrus et al. |
| 5,971,949 A | 10/1999 | Levin et al. |
| 6,007,499 A | 12/1999 | Martin et al. |
| 6,042,556 A | 3/2000 | Beach et al. |
| 6,073,048 A | 6/2000 | Kieval et al. |
| 6,077,225 A | 6/2000 | Brock-Fisher |
| 6,117,101 A | 9/2000 | Diederich et al. |
| 6,119,041 A | 9/2000 | Pomeranz et al. |
| 6,120,442 A * | 9/2000 | Hickey ................ A61B 5/0215 600/587 |
| 6,165,127 A | 12/2000 | Crowley |
| 6,210,393 B1 | 4/2001 | Brisken |
| 6,216,041 B1 | 4/2001 | Tierney et al. |
| 6,235,024 B1 | 5/2001 | Tu |
| 6,261,233 B1 * | 7/2001 | Kantorovich ............ A61B 8/06 600/454 |
| 6,296,619 B1 | 10/2001 | Brisken et al. |
| 6,379,320 B1 | 4/2002 | Lafon et al. |
| 6,428,477 B1 | 8/2002 | Mason |
| 6,451,013 B1 | 9/2002 | Bays et al. |
| 6,500,121 B1 | 12/2002 | Slayton et al. |
| 6,511,428 B1 | 1/2003 | Azuma et al. |
| 6,511,436 B1 | 1/2003 | Asmar |
| 6,514,249 B1 | 2/2003 | Maguire et al. |
| 6,524,271 B2 | 2/2003 | Brisken et al. |
| 6,527,759 B1 | 3/2003 | Tachibana et al. |
| 6,547,788 B1 | 4/2003 | Maguire et al. |
| 6,599,288 B2 | 7/2003 | Maguire et al. |
| 6,607,502 B1 | 8/2003 | Maguire et al. |
| 6,623,687 B1 | 9/2003 | Gervasi et al. |
| 6,645,147 B1 | 11/2003 | Jackson et al. |
| 6,740,040 B1 | 5/2004 | Mandrusov et al. |
| 6,752,805 B2 | 6/2004 | Maguire et al. |
| 6,953,460 B2 | 10/2005 | Maguire et al. |
| 6,955,173 B2 | 10/2005 | Lesh |
| 6,978,174 B2 | 12/2005 | Gelfand et al. |
| 7,001,336 B2 | 2/2006 | Mandrusov et al. |
| 7,037,271 B2 | 5/2006 | Crowley |
| 7,084,004 B2 | 8/2006 | Vaiyapuri et al. |
| 7,156,816 B2 | 1/2007 | Schwartz et al. |
| 7,162,303 B2 | 1/2007 | Levin et al. |
| 7,166,098 B1 | 1/2007 | Steward et al. |
| 7,220,233 B2 | 5/2007 | Nita et al. |
| 7,220,258 B2 | 5/2007 | Myhr |
| 7,220,261 B2 | 5/2007 | Truckai et al. |
| 7,285,116 B2 | 10/2007 | De la Rama et al. |
| 7,326,201 B2 | 2/2008 | Fjield et al. |
| 7,341,583 B2 | 3/2008 | Shiono et al. |
| 7,344,529 B2 | 3/2008 | Torchia et al. |
| 7,347,859 B2 | 3/2008 | Garabedian et al. |
| 7,410,486 B2 | 8/2008 | Fuimaono et al. |
| 7,460,369 B1 | 12/2008 | Blish, II |
| 7,470,241 B2 | 12/2008 | Weng et al. |
| 7,479,106 B2 | 1/2009 | Banik et al. |
| 7,510,536 B2 | 3/2009 | Foley et al. |
| 7,538,425 B2 | 5/2009 | Myers et al. |
| RE40,815 E | 6/2009 | Kudaravalli et al. |
| 7,540,846 B2 | 6/2009 | Harhen et al. |
| 7,540,870 B2 | 6/2009 | Babaev |
| 7,563,260 B2 | 7/2009 | Whitmore et al. |
| 7,617,005 B2 | 11/2009 | Demarais et al. |
| 7,620,451 B2 | 11/2009 | Demarais et al. |
| 7,621,929 B2 | 11/2009 | Nita et al. |
| 7,647,115 B2 | 1/2010 | Levin et al. |
| 7,653,438 B2 | 1/2010 | Deem et al. |
| 7,655,005 B2 | 2/2010 | Bhola |
| 7,678,104 B2 | 3/2010 | Keidar |
| 7,704,212 B2 | 4/2010 | Wekell et al. |
| 7,713,210 B2 | 5/2010 | Byrd et al. |
| 7,717,948 B2 | 5/2010 | Demarais et al. |
| 7,727,228 B2 | 6/2010 | Abboud et al. |
| 7,736,317 B2 | 6/2010 | Stephens et al. |
| 7,756,583 B2 | 7/2010 | Demarais et al. |
| 7,762,954 B2 | 7/2010 | Nix et al. |
| 7,771,372 B2 | 8/2010 | Wilson |
| 7,819,826 B2 * | 10/2010 | Diederich .............. A61B 18/04 601/3 |
| 7,819,868 B2 | 10/2010 | Cao et al. |
| 7,824,348 B2 | 11/2010 | Barthe et al. |
| 7,850,683 B2 | 12/2010 | Elkins et al. |
| 7,850,685 B2 | 12/2010 | Kunis et al. |
| 7,853,333 B2 | 12/2010 | Demarais |
| 7,854,733 B2 | 12/2010 | Govari |
| 7,883,506 B2 | 2/2011 | McIntyre et al. |
| 7,940,969 B2 | 5/2011 | Nair et al. |
| 8,216,216 B2 | 7/2012 | Warnking et al. |
| 8,221,402 B2 | 7/2012 | Francischelli et al. |
| 8,401,667 B2 | 3/2013 | Gustus et al. |
| 8,419,729 B2 | 4/2013 | Ibrahim et al. |
| 8,540,662 B2 | 9/2013 | Stehr et al. |
| 8,568,403 B2 | 10/2013 | Soltesz et al. |
| 8,585,695 B2 | 11/2013 | Shih |
| 8,715,209 B2 | 3/2014 | Gertner |
| 8,974,446 B2 | 3/2015 | Nguyen et al. |
| 10,368,893 B2 | 4/2019 | Sverdlik et al. |
| 11,318,331 B2 | 5/2022 | Shabtay |
| 2001/0007940 A1 | 7/2001 | Tu et al. |
| 2001/0014780 A1 | 8/2001 | Martin et al. |
| 2001/0053885 A1 | 12/2001 | Gielen et al. |
| 2002/0002371 A1 | 1/2002 | Acker et al. |
| 2002/0016624 A1 | 2/2002 | Patterson et al. |
| 2002/0019627 A1 | 2/2002 | Maguire et al. |

(56) References Cited

U.S. PATENT DOCUMENTS

| | | |
|---|---|---|
| 2002/0022833 A1 | 2/2002 | Maguire et al. |
| 2002/0026127 A1 | 2/2002 | Balbierz et al. |
| 2002/0048310 A1 | 4/2002 | Heuser |
| 2002/0055754 A1 | 5/2002 | Ranucci et al. |
| 2002/0065512 A1 | 5/2002 | Fjield et al. |
| 2002/0077643 A1 | 6/2002 | Rabiner et al. |
| 2002/0169394 A1 | 11/2002 | Eppstein et al. |
| 2002/0188218 A1 | 12/2002 | Lipman |
| 2003/0013968 A1 | 1/2003 | Fjield et al. |
| 2003/0092667 A1 | 5/2003 | Tachibana et al. |
| 2003/0125726 A1 | 7/2003 | Maguire et al. |
| 2003/0151417 A1 | 8/2003 | Koen |
| 2003/0158545 A1 | 8/2003 | Hovda et al. |
| 2003/0163190 A1 | 8/2003 | LaFont et al. |
| 2003/0181901 A1 | 9/2003 | Maguire et al. |
| 2003/0195496 A1 | 10/2003 | Maguire et al. |
| 2003/0199747 A1 | 10/2003 | Michlitsch et al. |
| 2003/0199768 A1 | 10/2003 | Cespededs et al. |
| 2004/0006333 A1 | 1/2004 | Arnold et al. |
| 2004/0019687 A1 | 1/2004 | Ozawa et al. |
| 2004/0073660 A1 | 4/2004 | Toomey |
| 2004/0082859 A1 | 4/2004 | Schaer |
| 2004/0102361 A1 | 5/2004 | Bodin |
| 2004/0102769 A1 | 5/2004 | Schwartz et al. |
| 2004/0143358 A1 | 7/2004 | Silverbrook |
| 2005/0015079 A1 | 1/2005 | Keider |
| 2005/0020967 A1 | 1/2005 | Ono |
| 2005/0096542 A1 | 5/2005 | Weng et al. |
| 2005/0096647 A1 | 5/2005 | Steinke et al. |
| 2005/0215946 A1 | 9/2005 | Hansmann et al. |
| 2005/0240170 A1 | 10/2005 | Zhang et al. |
| 2005/0288730 A1 | 12/2005 | Deem et al. |
| 2006/0009753 A1 | 1/2006 | Fjield et al. |
| 2006/0052774 A1 | 3/2006 | Garrison et al. |
| 2006/0058711 A1 | 3/2006 | Harhen et al. |
| 2006/0079816 A1 | 4/2006 | Barthe et al. |
| 2006/0084966 A1 | 4/2006 | Maguire et al. |
| 2006/0173387 A1 | 8/2006 | Hansmann et al. |
| 2006/0229594 A1 | 10/2006 | Francischelli et al. |
| 2006/0241442 A1 | 10/2006 | Barthe et al. |
| 2006/0241739 A1 | 10/2006 | Besselink et al. |
| 2006/0264809 A1 | 11/2006 | Hansmann et al. |
| 2006/0287604 A1* | 12/2006 | Hickey ............... A61B 7/026 600/528 |
| 2007/0043297 A1 | 2/2007 | Miyazawa |
| 2007/0088346 A1 | 4/2007 | Mirizzi et al. |
| 2007/0142831 A1 | 6/2007 | Shadduck |
| 2007/0142879 A1 | 6/2007 | Greenberg et al. |
| 2007/0167824 A1 | 7/2007 | Lee et al. |
| 2007/0203479 A1 | 8/2007 | Auth et al. |
| 2007/0222339 A1 | 9/2007 | Lukacs et al. |
| 2007/0225619 A1 | 9/2007 | Rabiner et al. |
| 2007/0233057 A1 | 10/2007 | Konishi |
| 2007/0249997 A1 | 10/2007 | Goodson, IV et al. |
| 2007/0282407 A1 | 12/2007 | Demarais et al. |
| 2008/0039745 A1 | 2/2008 | Babaev |
| 2008/0077202 A1 | 3/2008 | Levinson |
| 2008/0086073 A1 | 4/2008 | McDaniel |
| 2008/0114354 A1 | 5/2008 | Whayne et al. |
| 2008/0125829 A1 | 5/2008 | Velasco et al. |
| 2008/0139971 A1 | 6/2008 | Lockhart |
| 2008/0146924 A1 | 6/2008 | Smith et al. |
| 2008/0171934 A1 | 7/2008 | Greenan et al. |
| 2008/0179736 A1 | 7/2008 | Hartwell et al. |
| 2008/0183110 A1 | 7/2008 | Davenport et al. |
| 2008/0195000 A1 | 8/2008 | Spooner et al. |
| 2008/0213331 A1* | 9/2008 | Gelfand ............... A61K 31/135 604/20 |
| 2008/0214966 A1 | 9/2008 | Slayton et al. |
| 2008/0215039 A1 | 9/2008 | Slatkine et al. |
| 2008/0228111 A1 | 9/2008 | Nita |
| 2008/0249518 A1 | 10/2008 | Warnking et al. |
| 2008/0281297 A1 | 11/2008 | Pesach et al. |
| 2008/0300571 A1 | 12/2008 | LePivert |
| 2008/0300655 A1 | 12/2008 | Cholette |
| 2008/0312643 A1 | 12/2008 | Kania et al. |
| 2009/0018446 A1 | 1/2009 | Medan et al. |
| 2009/0036914 A1 | 2/2009 | Houser |
| 2009/0093737 A1 | 4/2009 | Chomas et al. |
| 2009/0131930 A1 | 5/2009 | Gelbart et al. |
| 2009/0149782 A1 | 6/2009 | Cohen et al. |
| 2009/0163807 A1 | 6/2009 | Sliwa |
| 2009/0216246 A1 | 8/2009 | Nita et al. |
| 2009/0221939 A1 | 9/2009 | Demarais et al. |
| 2009/0221955 A1 | 9/2009 | Babaev |
| 2009/0254078 A1 | 10/2009 | Just et al. |
| 2009/0281478 A1 | 11/2009 | Duke |
| 2009/0299360 A1 | 12/2009 | Ormsby |
| 2010/0036293 A1 | 2/2010 | Isola et al. |
| 2010/0081933 A1 | 4/2010 | Sverdlik et al. |
| 2010/0091112 A1 | 4/2010 | Veeser et al. |
| 2010/0114082 A1 | 5/2010 | Sharma |
| 2010/0125198 A1 | 5/2010 | Thapliyal et al. |
| 2010/0130892 A1 | 5/2010 | Warnking |
| 2010/0137860 A1 | 6/2010 | Demarais et al. |
| 2010/0152625 A1 | 6/2010 | Milo |
| 2010/0168624 A1 | 7/2010 | Sliwa |
| 2010/0168649 A1 | 7/2010 | Schwartz et al. |
| 2010/0168731 A1* | 7/2010 | Wu ............... A61B 18/1206 606/33 |
| 2010/0185156 A1 | 7/2010 | Kanner et al. |
| 2010/0191112 A1 | 7/2010 | Demarais et al. |
| 2010/0198040 A1 | 8/2010 | Friedman et al. |
| 2010/0210946 A1 | 8/2010 | Harada et al. |
| 2010/0222851 A1 | 9/2010 | Deem et al. |
| 2010/0228162 A1 | 9/2010 | Sliwa et al. |
| 2010/0262014 A1 | 10/2010 | Huang |
| 2010/0331686 A1 | 12/2010 | Hossack et al. |
| 2010/0331950 A1 | 12/2010 | Strommer |
| 2011/0009779 A1 | 1/2011 | Romano et al. |
| 2011/0028962 A1 | 2/2011 | Werneth et al. |
| 2011/0034809 A1 | 2/2011 | Eberle et al. |
| 2011/0066217 A1 | 3/2011 | Diller et al. |
| 2011/0092781 A1 | 4/2011 | Gertner |
| 2011/0092880 A1 | 4/2011 | Gertner |
| 2011/0106132 A1 | 5/2011 | Barbut et al. |
| 2011/0112400 A1* | 5/2011 | Emery ............... A61N 7/00 601/3 |
| 2011/0178441 A1 | 7/2011 | Tyler |
| 2011/0201973 A1 | 8/2011 | Stephens et al. |
| 2011/0257563 A1 | 10/2011 | Thapliyal et al. |
| 2011/0264075 A1* | 10/2011 | Leung ............... A61B 18/20 607/116 |
| 2011/0264086 A1 | 10/2011 | Ingle |
| 2011/0270247 A1 | 11/2011 | Sherman |
| 2011/0282203 A1 | 11/2011 | Tsoref et al. |
| 2011/0282249 A1 | 11/2011 | Tsoref et al. |
| 2011/0301662 A1* | 12/2011 | Bar-Yoseph ....... A61N 1/36007 607/40 |
| 2011/0319765 A1 | 12/2011 | Gertner et al. |
| 2012/0016273 A1 | 1/2012 | Diederich |
| 2012/0053577 A1 | 3/2012 | Lee et al. |
| 2012/0065494 A1 | 3/2012 | Gertner et al. |
| 2012/0095335 A1 | 4/2012 | Sverdlik et al. |
| 2012/0095371 A1 | 4/2012 | Sverdlik et al. |
| 2012/0095372 A1 | 4/2012 | Sverdlik et al. |
| 2012/0123243 A1 | 5/2012 | Hastings |
| 2012/0123270 A1 | 5/2012 | Klee et al. |
| 2012/0203098 A1* | 8/2012 | Raju ............... A61N 7/02 601/3 |
| 2012/0209116 A1 | 8/2012 | Hossack et al. |
| 2012/0215106 A1 | 8/2012 | Sverdlik et al. |
| 2012/0232409 A1 | 9/2012 | Stahmann et al. |
| 2012/0232436 A1 | 9/2012 | Warnking |
| 2012/0265227 A1 | 10/2012 | Sverdlik et al. |
| 2012/0268886 A1 | 10/2012 | Leontiev et al. |
| 2012/0283605 A1 | 11/2012 | Lewis, Jr. |
| 2012/0310233 A1 | 12/2012 | Dimmer et al. |
| 2012/0316559 A1 | 12/2012 | Mayse et al. |
| 2013/0072928 A1 | 3/2013 | Schaer |
| 2013/0123670 A1 | 5/2013 | Smith |
| 2013/0131668 A1 | 5/2013 | Schaer |
| 2013/0197555 A1 | 8/2013 | Schaer |
| 2013/0204068 A1 | 8/2013 | Gnanashanmugam et al. |

(56) References Cited

U.S. PATENT DOCUMENTS

| | | | |
|---|---|---|---|
| 2013/0204167 A1 | 8/2013 | Sverdlik et al. | |
| 2013/0204242 A1 | 8/2013 | Sverdlik et al. | |
| 2013/0207519 A1 | 8/2013 | Chaggares et al. | |
| 2013/0211292 A1 | 8/2013 | Sverdlik et al. | |
| 2013/0211396 A1 | 8/2013 | Sverdlik et al. | |
| 2013/0211437 A1 | 8/2013 | Sverdlik et al. | |
| 2013/0218054 A1 | 8/2013 | Sverdlik et al. | |
| 2013/0218068 A1 | 8/2013 | Sverdlik et al. | |
| 2013/0225595 A1 | 8/2013 | Gillies et al. | |
| 2013/0226040 A1 | 8/2013 | Michael et al. | |
| 2013/0267875 A1 | 10/2013 | Thapliyal et al. | |
| 2013/0274607 A1* | 10/2013 | Anand | A61B 8/54 600/454 |
| 2013/0296836 A1 | 11/2013 | Barbut et al. | |
| 2013/0310822 A1 | 11/2013 | Mayse et al. | |
| 2014/0005706 A1 | 1/2014 | Gelfand et al. | |
| 2014/0012133 A1* | 1/2014 | Sverdlik | A61B 8/485 600/587 |
| 2014/0024975 A1 | 1/2014 | Little et al. | |
| 2014/0039286 A1 | 2/2014 | Hoffer | |
| 2014/0039477 A1 | 2/2014 | Sverdlik et al. | |
| 2014/0058294 A1 | 2/2014 | Gross et al. | |
| 2014/0074076 A1 | 3/2014 | Gertner | |
| 2014/0088585 A1 | 3/2014 | Hill et al. | |
| 2014/0114215 A1* | 4/2014 | Melder | A61B 18/20 604/20 |
| 2014/0163540 A1 | 6/2014 | Iyer et al. | |
| 2014/0163652 A1 | 6/2014 | Witzel et al. | |
| 2014/0180197 A1 | 6/2014 | Sverdlik et al. | |
| 2014/0180277 A1 | 6/2014 | Chen | |
| 2014/0194866 A1 | 7/2014 | Wang | |
| 2014/0255647 A1 | 9/2014 | Johnson et al. | |
| 2014/0257262 A1 | 9/2014 | Carpentier et al. | |
| 2014/0276135 A1 | 9/2014 | Agah et al. | |
| 2014/0359111 A1 | 12/2014 | Hilmo et al. | |
| 2015/0057599 A1 | 2/2015 | Chen | |
| 2015/0073400 A1 | 3/2015 | Sverdlik et al. | |
| 2015/0112234 A1 | 4/2015 | McCaffrey et al. | |
| 2015/0190660 A1 | 7/2015 | Sarge et al. | |
| 2015/0272668 A1 | 10/2015 | Chen | |
| 2016/0059044 A1 | 3/2016 | Gertner | |
| 2016/0059489 A1 | 3/2016 | Wang et al. | |
| 2016/0113699 A1* | 4/2016 | Sverdlik | A61N 7/022 606/27 |
| 2016/0374710 A1 | 12/2016 | Sinelnikov et al. | |
| 2017/0027645 A1 | 2/2017 | Ben Oren et al. | |
| 2017/0050374 A1 | 2/2017 | Minardi et al. | |
| 2017/0120333 A1 | 5/2017 | DeMuth et al. | |
| 2017/0246482 A1 | 8/2017 | Hananel et al. | |
| 2017/0312021 A1 | 11/2017 | Pilcher et al. | |
| 2017/0354461 A1 | 12/2017 | Rothman et al. | |
| 2018/0055988 A1 | 3/2018 | Brun | |
| 2018/0326227 A1 | 11/2018 | Sverdlik et al. | |
| 2019/0290350 A1 | 9/2019 | Sverdlik et al. | |
| 2019/0308003 A1 | 10/2019 | Sverdlik et al. | |
| 2019/0366130 A1 | 12/2019 | Sverdlik et al. | |
| 2020/0238107 A1 | 7/2020 | Shabtay et al. | |
| 2020/0368244 A1 | 11/2020 | Shabtay et al. | |
| 2021/0178194 A1 | 6/2021 | Sverdlik et al. | |
| 2022/0241617 A1 | 8/2022 | Shabtay et al. | |
| 2023/0389954 A1 | 12/2023 | Sverdlik et al. | |

FOREIGN PATENT DOCUMENTS

| | | |
|---|---|---|
| CN | 101610735 | 12/2009 |
| CN | 101820820 | 9/2010 |
| EP | 1384445 | 1/2004 |
| EP | 1424100 | 6/2004 |
| EP | 1799302 | 3/2006 |
| EP | 1769759 | 4/2007 |
| EP | 1802370 | 7/2007 |
| EP | 2092957 | 8/2009 |
| EP | 2218479 | 8/2010 |
| EP | 2455133 | 5/2012 |
| JP | 07-227394 | 8/1995 |
| JP | 09-122139 | 5/1997 |
| JP | 10-248854 | 9/1998 |
| JP | 2008-536562 | 9/2008 |
| JP | 2010-517695 | 5/2010 |
| JP | 2019-018526 | 2/2019 |
| WO | WO 91/10405 | 7/1991 |
| WO | WO 99/16366 | 4/1999 |
| WO | WO 00/67648 | 10/2000 |
| WO | WO 01/45550 | 6/2001 |
| WO | WO 02/096501 | 12/2002 |
| WO | WO 2004/054448 | 7/2004 |
| WO | WO 2006/022790 | 3/2006 |
| WO | WO 2006/041847 | 4/2006 |
| WO | WO 2006/041881 | 4/2006 |
| WO | WO 2006/042163 | 4/2006 |
| WO | WO 2007/001981 | 1/2007 |
| WO | WO 2007/078997 | 7/2007 |
| WO | WO 2007/115307 | 10/2007 |
| WO | WO 2007/127176 | 11/2007 |
| WO | WO 2008/003058 | 1/2008 |
| WO | WO 2008/098101 | 8/2008 |
| WO | WO 2008/102363 | 8/2008 |
| WO | WO 2010/009473 | 1/2010 |
| WO | WO 2010/118307 | 10/2010 |
| WO | WO 2011/053757 | 5/2011 |
| WO | WO 2011/060200 | 5/2011 |
| WO | WO 2011/075328 | 6/2011 |
| WO | WO 2012/052920 | 4/2012 |
| WO | WO 2012/052921 | 4/2012 |
| WO | WO 2012/052922 | 4/2012 |
| WO | WO 2012/052924 | 4/2012 |
| WO | WO 2012/052925 | 4/2012 |
| WO | WO 2012/052926 | 4/2012 |
| WO | WO 2012/052927 | 4/2012 |
| WO | WO 2012/082927 | 4/2012 |
| WO | WO-2012052926 A2 * | 4/2012 ......... A61B 17/22012 |
| WO | WO 2012/061713 | 5/2012 |
| WO | WO 2013/030743 | 3/2013 |
| WO | WO 2013/111136 | 8/2013 |
| WO | WO 2013/134479 | 9/2013 |
| WO | WO 2013/157009 | 10/2013 |
| WO | WO 2013/157011 | 10/2013 |
| WO | WO 2013/162694 | 10/2013 |
| WO | WO 2014/141052 | 9/2014 |
| WO | WO 2014/188430 | 11/2014 |
| WO | WO 2016/084081 | 6/2016 |
| WO | WO 2016/084081 A8 | 6/2017 |
| WO | WO 2018/173052 | 9/2018 |
| WO | WO 2018/173053 | 9/2018 |

OTHER PUBLICATIONS

Official Action Dated Mar. 3, 2023 from the US Patent and Trademark Office Re. U.S. Appl. No. 16/540,191. (56 pages).
Cheever "An Overview of Pulmonary Arterial Hypertension: Risks, Pathogenesis, Clinical Manifestations, and Management", The Journal of Cardiovascular Nursing 20(2): 108-116, Mar. 2005. Abstract.
Advisory Action Before the Filing of An Appeal Brief Dated Feb. 4, 2019 From the US Patent and Trademark Office Re. U.S. Appl. No. 14/190,113. (6 pages).
Advisory Action Dated Jun. 16, 2020 from the US Patent and Trademark Office Re. U.S. Appl. No. 13/449,539. (5 pages).
Applicant-Initiated Interview Summary Dated Apr. 2, 2019 From the US Patent and Trademark Office Re. U.S. Appl. No. 13/905,224. (3 pages).
Applicant-Initiated Interview Summary Dated Jan. 4, 2016 From the US Patent and Trademark Office Re. U.S. Appl. No. 13/449,539.
Applicant-Initiated Interview Summary Dated Jul. 14, 2016 From the US Patent and Trademark Office Re. U.S. Appl. No. 13/449,539.
Applicant-Initiated Interview Summary Dated Nov. 14, 2018 From the US Patent and Trademark Office Re. U.S. Appl. No. 13/449,539. (3 pages).
Applicant-Initiated Interview Summary Dated Jan. 21, 2015 From the US Patent and Trademark Office Re. U.S. Appl. No. 13/449,539.
Applicant-Initiated Interview Summary Dated Feb. 22, 2016 From the US Patent and Trademark Office Re. U.S. Appl. No. 13/880,066.

(56) References Cited

OTHER PUBLICATIONS

Applicant-Initiated Interview Summary Dated Jan. 24, 2014 From the US Patent and Trademark Office Re. U.S. Appl. No. 13/449,539.
Applicant-Initiated Interview Summary Dated Apr. 25, 2018 From the US Patent and Trademark Office Re. U.S. Appl. No. 14/394,276. (3 pages).
Applicant-Initiated Interview Summary Dated Sep. 28, 2016 From the US Patent and Trademark Office Re. U.S. Appl. No. 13/905,224.
Communication Pursuant to Article 94(3) EPC Dated Dec. 2, 2020 From the European Patent Office Re. Application No. 15862313.2. (9 Pages).
Communication Pursuant to Article 94(3) EPC Dated Nov. 4, 2014 From the European Patent Office Re. Application No. 11833950.6.
Communication Pursuant to Article 94(3) EPC Dated Feb. 8, 2016 From the European Patent Office Re. Application No. 11833950.6.
Communication Pursuant to Article 94(3) EPC Dated Apr. 10, 2015 From the European Patent Office Re. Application No. 11782222.1.
Communication Pursuant to Article 94(3) EPC Dated Jun. 10, 2014 From the European Patent Office Re. Application No. 11782476.3.
Communication Pursuant to Article 94(3) EPC Dated Jun. 10, 2014 From the European Patent Office Re. Application No. 11784782.2.
Communication Pursuant to Article 94(3) EPC Dated Apr. 14, 2014 From the European Patent Office Re. Application No. 11782221.3.
Communication Pursuant to Article 94(3) EPC Dated Jul. 20, 2016 From the European Patent Office Re. Application No. 11782221.3.
Communication Pursuant to Article 94(3) EPC Dated Sep. 26, 2014 From the European Patent Office Re. Application No. 11782222.1.
Communication Pursuant to Article 94(3) EPC Dated Jul. 27, 2016 From the European Patent Office Re. Application No. 11782222.1.
Communication Pursuant to Article 94(3) EPC Dated Oct. 30, 2014 From the European Patent Office Re. Application No. 11782221.3.
Communication Pursuant to Rule 164(1) EPC: Supplementary Partial European Search Report and the European Provisional Opinion Dated May 18, 2018 From the European Patent Office Re. Application No. 15862313.2. (15 Pages).
Decision of Rejection Dated Sep. 2, 2022 From the China National Intellectual Property Administration Re. Application No. 201880031962 and its Summary in English. (4 Pages).
Decision of Rejection Dated Apr. 28, 2016 From the Japanese Patent Office Re. Application No. 2013-534435 and Its Machine Translation in English.
Final Official Action Dated Jun. 3, 2021 From the US Patent and Trademark Office Re. U.S. Appl. No. 13/905,224. (17 Pages).
Final Official Action Dated Jul. 12, 2022 from US Patent and Trademark Office Re. U.S. Appl. No. 16/494,322. (28 pages).
Final Official Action Dated Sep. 15, 2022 from US Patent and Trademark Office Re. U.S. Appl. No. 16/451,087. (13 pages).
International Preliminary Report on Patentability Dated May 2, 2013 From the International Bureau of WIPO Re. Application No. PCT/IB2011/054634.
International Preliminary Report on Patentability Dated May 2, 2013 From the International Bureau of WIPO Re. Application No. PCT/IB2011/054635.
International Preliminary Report on Patentability Dated May 2, 2013 From the International Bureau of WIPO Re. Application No. PCT/IB2011/054636.
International Preliminary Report on Patentability Dated May 2, 2013 From the International Bureau of WIPO Re. Application No. PCT/IB2011/054638.
International Preliminary Report on Patentability Dated May 2, 2013 From the International Bureau of WIPO Re. Application No. PCT/IB2011/054639.
International Preliminary Report on Patentability Dated May 2, 2013 From the International Bureau of WIPO Re. Application No. PCT/IB2011/054640.
International Preliminary Report on Patentability Dated May 2, 2013 From the International Bureau of WIPO Re. Application No. PCT/IB2011/054641.
International Preliminary Report on Patentability Dated Dec. 3, 2015 From the International Bureau of WIPO Re. Application No. PCT/IL2014/050457.
International Preliminary Report on Patentability Dated Oct. 3, 2019 From the International Bureau of WIPO Re. Application No. PCT/IL2018/050321. (11 Pages).
International Preliminary Report on Patentability Dated Oct. 3, 2019 From the International Bureau of WIPO Re. Application No. PCT/IL2018/050322. (16 Pages).
International Preliminary Report on Patentability Dated Aug. 7, 2014 From the International Bureau of WIPO Re. Application No. PCT/IL2013/050068.
International Preliminary Report on Patentability Dated Jun. 8, 2017 From the International Bureau of WIPO Re. Application No. PCT/IL2015/051145. (16 Pages).
International Preliminary Report on Patentability Dated Oct. 30, 2014 From the International Bureau of WIPO Re. Application No. PCT/IL2013/050339.
International Preliminary Report on Patentability Dated Oct. 30, 2014 From the International Bureau of WIPO Re. Application No. PCT/IL2013/050341.
International Search Report and the Written Opinion Dated May 2, 2016 From the International Searching Authority Re. Application No. PCT/IL2015/051145.
International Search Report and the Written Opinion Dated Feb. 7, 2012 From the International Searching Authority Re. Application No. PCT/IB2011/054641.
International Search Report and the Written Opinion Dated Oct. 11, 2013 From the International Searching Authority Re. Application No. PCT/IL2013/050341.
International Search Report and the Written Opinion Dated Sep. 19, 2013 From the International Searching Authority Re. Application No. PCT/IL2013/050068.
International Search Report and the Written Opinion Dated Nov. 20, 2014 From the International Searching Authority Re. Application No. PCT/IL2014/050457.
International Search Report and the Written Opinion Dated Jun. 22, 2012 From the International Searching Authority Re. Application No. PCT/IB2011/054640.
International Search Report and the Written Opinion Dated Jan. 23, 2012 From the International Searching Authority Re. Application No. PCT/IB2011/054635.
International Search Report and the Written Opinion Dated Jan. 25, 2012 From the International Searching Authority Re. Application No. PCT/IB2011/054636.
International Search Report and the Written Opinion Dated Jan. 27, 2012 From the International Searching Authority Re. Application No. PCT/IB2011/054634.
International Search Report and the Written Opinion Dated Jan. 27, 2012 From the International Searching Authority Re. Application No. PCT/IB2011/054638.
International Search Report and the Written Opinion Dated Aug. 28, 2018 From the International Searching Authority Re. Application No. PCT/IL2018/050322. (40 Pages).
International Search Report and the Written Opinion Dated Aug. 29, 2018 From the International Searching Authority Re. Application No. PCT/IL2018/050321. (16 Pages).
International Search Report and the Written Opinion Dated Jan. 31, 2012 From the International Searching Authority Re. Application No. PCT/IB2011/054639.
Invitation Pursuant to Rule 137(4) EPC Dated Apr. 4, 2014 From the European Patent Office Re. Application No. 11785792.0.
Invitation Pursuant to Rule 137(4) EPC Dated Apr. 8, 2014 From the European Patent Office Re. Application No. 11782222.1.
Invitation Pursuant to Rule 137(4) EPC Dated Apr. 10, 2014 From the European Patent Office Re. Application No. 11782476.3.
Invitation Pursuant to Rule 137(4) EPC Dated Mar. 21, 2016 From the European Patent Office Re. Application No. 11782222.1.
Invitation to Pay Additional Fees Dated Sep. 3, 2013 From the International Searching Authority Re. Application No. PCT/IL2013/050339.

(56) References Cited

OTHER PUBLICATIONS

Invitation To Pay Additional Fees Dated Mar. 4, 2016 From the International Searching Authority Re. Application No. PCT/IL2015/051145.
Invitation to Pay Additional Fees Dated Sep. 4, 2014 From the International Searching Authority Re. Application No. PCT/IL2014/050457.
Invitation to Pay Additional Fees Dated Aug. 5, 2013 From the International Searching Authority Re. Application No. PCT/IL2013/050341.
Invitation to Pay Additional Fees Dated Apr. 17, 2012 From the International Searching Authority Re. Application No. PCT/IB2011/054640.
Invitation to Pay Additional Fees Dated Jun. 21, 2018 From the International Searching Authority Re. Application No. PCT/IL2018/050322. (3 Pages).
Invitation to Pay Additional Fees Dated Jul. 24, 2013 From the International Searching Authority Re. Application No. PCT/IL2013/050068.
Invitation to Pay Additional Fees Dated Jun. 25, 2018 From the International Searching Authority Re. Application No. PCT/IL2018/050321. (2 Pages).
Notice of Allowance Dated Mar. 6, 2019 From the US Patent and Trademark Office Re. U.S. Appl. No. 14/394,276. (11 Pages).
Notice of Allowance Dated Oct. 6, 2014 From the US Patent and Trademark Office Re. U.S. Appl. No. 13/880,061.
Notice of Allowance Dated Nov. 7, 2013 From the US Patent and Trademark Office Re. U.S. Appl. No. 13/049,013.
Notice of Allowance Dated Dec. 8, 2015 From the US Patent and Trademark Office Re. U.S. Appl. No. 14/049,238.
Notice of Allowance Dated Jan. 8, 2015 From the US Patent and Trademark Office Re. U.S. Appl. No. 13/880,061.
Notice of Allowance Dated Feb. 10, 2022 from US Patent and Trademark Office Re. U.S. Appl. No. 13/905,224. (8 pages).
Notice of Allowance Dated Aug. 11, 2020 from the US Patent and Trademark Office Re. U.S. Appl. No. 13/449,539. (11 pages).
Notice of Allowance Dated Sep. 14, 2016 From the US Patent and Trademark Office Re. U.S. Appl. No. 13/879,400.
Notice of Allowance Dated Jul. 18, 2016 From the US Patent and Trademark Office Re. U.S. Appl. No. 13/879,400.
Notice of Allowance Dated Jun. 21, 2013 From the US Patent and Trademark Office Re. U.S. Appl. No. 13/049,151.
Notice of Allowance Dated Sep. 23, 2020 from the US Patent and Trademark Office Re. U.S. Appl. No. 14/889,890. (8 pages).
Notice of Allowance Dated Mar. 26, 2019 From the US Patent and Trademark Office Re. U.S. Appl. No. 14/190,113. (8 pages).
Notice of Allowance Dated Dec. 29, 2021 from US Patent and Trademark Office Re. U.S. Appl. No. 16/494,321. (51 pages).
Notice of Non-Compliant Amendment Dated Sep. 23, 2015 From the US Patent and Trademark Office Re. U.S. Appl. No. 13/880,124.
Notice of Reason for Rejection Dated Aug. 25, 2015 From the Japanese Patent Office Re. Application No. 2013-534435.
Notification of Office Action and Search Report Dated Apr. 1, 2021 From the State Intellectual Property Office of the People's Republic of China Re. Application No. 201880031396.2 and Its Translation of Office Action Into English. (9 Pages).
Notification of Office Action and Search Report Dated Dec. 1, 2014 From the State Intellectual Property Office of the People's Republic of China Re. Application No. 201180060862.8.
Notification of Office Action and Search Report Dated Mar. 14, 2022 From the State Intellectual Property Office of the People's Republic of China Re. Application No. 20188003196.2 and Its Translation of Office Action Into English. (15 Pages).
Office Action Dated Jul. 30, 2014 From the State Intellectual Property Office of the People's Republic of China Re. Application No. 201180060741.3 and Its Summary in English.
Official Action Dated Aug. 2, 2021 from the US Patent and Trademark Office Re. U.S. Appl. No. 16/494,321. (10 pages).
Official Action Dated Jul. 2, 2015 From the US Patent and Trademark Office Re. U.S. Appl. No. 13/879,400.
Official Action Dated Dec. 3, 2014 From the US Patent and Trademark Office Re. U.S. Appl. No. 13/462,956.
Official Action Dated Jun. 3, 2016 From the US Patent and Trademark Office Re. U.S. Appl. No. 13/880,066.
Official Action Dated Jun. 3, 2019 From the US Patent and Trademark Office Re. U.S. Appl. No. 13/449,539. (13 Pages).
Official Action Dated Nov. 3, 2017 From the US Patent and Trademark Office Re. U.S. Appl. No. 14/394,276. (11 pages).
Official Action Dated Nov. 4, 2014 From the US Patent and Trademark Office Re. U.S. Appl. No. 13/879,400.
Official Action Dated Aug. 5, 2015 From the US Patent and Trademark Office Re. U.S. Appl. No. 13/905,224.
Official Action Dated Jan. 5, 2016 From the US Patent and Trademark Office Re. U.S. Appl. No. 13/880,124.
Official Action Dated Jun. 5, 2015 From the US Patent and Trademark Office Re. U.S. Appl. No. 14/049,238.
Official Action Dated Nov. 5, 2014 From the US Patent and Trademark Office Re. U.S. Appl. No. 13/049,022.
Official Action Dated Feb. 6, 2015 From the US Patent and Trademark Office Re. U.S. Appl. No. 14/190,113.
Official Action Dated Jan. 6, 2017 From the US Patent and Trademark Office Re. U.S. Appl. No. 14/190,113. (11 pages).
Official Action Dated Oct. 7, 2014 From the US Patent and Trademark Office Re. U.S. Appl. No. 13/880,109.
Official Action Dated May 8, 2013 From the US Patent and Trademark Office Re. U.S. Appl. No. 13/462,956.
Official Action Dated Aug. 10, 2018 From the US Patent and Trademark Office Re. U.S. Appl. No. 14/190,113. (11 pages).
Official Action Dated Jun. 10, 2016 From the US Patent and Trademark Office Re. U.S. Appl. No. 14/190,113.
Official Action Dated Mar. 10, 2016 From the US Patent and Trademark Office Re. U.S. Appl. No. 13/449,539.
Official Action Dated Sep. 10, 2014 From the US Patent and Trademark Office Re. U.S. Appl. No. 14/049,238.
Official Action Dated Mar. 11, 2021 from the US Patent and Trademark Office Re. U.S. Appl. No. 16/494,321. (7 pages).
Official Action Dated Oct. 11, 2018 From the US Patent and Trademark Office Re. U.S. Appl. No. 14/394,276. (200 Pages).
Official Action Dated Sep. 11, 2015 From the US Patent and Trademark Office Re. U.S. Appl. No. 13/880,066.
Official Action Dated Apr. 13, 2020 from the US Patent and Trademark Office Re. U.S. Appl. No. 14/889,890. (23 pages).
Official Action Dated Aug. 13, 2020 from the US Patent and Trademark Office Re. U.S. Appl. No. 13/905,224. (24 pages).
Official Action Dated Apr. 14, 2014 From the US Patent and Trademark Office Re. U.S. Appl. No. 13/879,400.
Official Action Dated Aug. 14, 2015 From the US Patent and Trademark Office Re. U.S. Appl. No. 13/449,539.
Official Action Dated May 16, 2019 From the US Patent and Trademark Office Re. U.S. Appl. No. 15/529,137. (11 pages).
Official Action Dated Oct. 16, 2019 From the US Patent and Trademark Office Re. U.S. Appl. No. 13/449,539.(8 Pages).
Official Action Dated Jul. 17, 2013 From the US Patent and Trademark Office Re. U.S. Appl. No. 13/049,013.
Official Action Dated Nov. 17, 2017 From the US Patent and Trademark Office Re. U.S. Appl. No. 13/905,224. (19 pages).
Official Action Dated Dec. 19, 2013 From the US Patent and Trademark Office Re. U.S. Appl. No. 13/049,022.
Official Action Dated Mar. 20, 2014 From the US Patent and Trademark Office Re. U.S. Appl. No. 13/449,539.
Official Action Dated Oct. 20, 2017 From the US Patent and Trademark Office Re. U.S. Appl. No. 14/190,113. (7 pages).
Official Action Dated Apr. 21, 2017 From the US Patent and Trademark Office Re. U.S. Appl. No. 14/394,276. (13 pages).
Official Action Dated Feb. 21, 2019 From the US Patent and Trademark Office Re. U.S. Appl. No. 14/889,890. (19 pages).
Official Action Dated Jan. 21, 2022 From the US Patent and Trademark Office Re. U.S. Appl. No. 16/451,087. (150 Pages).
Official Action Dated Jun. 21, 2018 From the US Patent and Trademark Office Re. U.S. Appl. No. 13/449,539. (8 pages).
Official Action Dated Apr. 23, 2014 From the US Patent and Trademark Office Re. U.S. Appl. No. 13/880,061.

(56) References Cited

OTHER PUBLICATIONS

Official Action Dated Sep. 23, 2022 from US Patent and Trademark Office Re. U.S. Appl. No. 16/540,191. (14 pages).
Official Action Dated Oct. 24, 2012 From the US Patent and Trademark Office Re. U.S. Appl. No. 13/049,013.
Official Action Dated Oct. 24, 2019 From the US Patent and Trademark Office Re. U.S. Appl. No. 14/889,890. (54 pages).
Official Action Dated Sep. 25, 2013 From the US Patent and Trademark Office Re. U.S. Appl. No. 13/462,956.
Official Action Dated Sep. 25, 2015 From the US Patent and Trademark Office Re. U.S. Appl. No. 14/190,113.
Official Action Dated Jul. 26, 2016 From the US Patent and Trademark Office Re. U.S. Appl. No. 13/880,124.
Official Action Dated Dec. 27, 2016 From the US Patent and Trademark Office Re. U.S. Appl. No. 13/449,539. (13 pages).
Official Action Dated Apr. 29, 2016 From the US Patent and Trademark Office Re. U.S. Appl. No. 13/905,224.
Official Action Dated Aug. 29, 2013 From the US Patent and Trademark Office Re. U.S. Appl. No. 13/449,539.
Official Action Dated Jan. 29, 2013 From the US Patent and Trademark Office Re. U.S. Appl. No. 13/049,151.
Official Action Dated Aug. 31, 2021 from the US Patent and Trademark Office Re. U.S. Appl. No. 16/494,322. (27 pages).
Official Action Dated Oct. 31, 2018 From the US Patent and Trademark Office Re. U.S. Appl. No. 13/905,224. (23 pages).
Restriction Official Action Dated Jan. 4, 2019 From the US Patent and Trademark Office Re. U.S. Appl. No. 15/529,137. (8 pages).
Restriction Official Action Dated Oct. 5, 2012 From the US Patent and Trademark Office Re. U.S. Appl. No. 13/049,151.
Restriction Official Action Dated Jul. 7, 2014 From the US Patent and Trademark Office Re. U.S. Appl. No. 14/049,238.
Restriction Official Action Dated Apr. 14, 2015 From the US Patent and Trademark Office Re. U.S. Appl. No. 13/880,124.
Restriction Official Action Dated Nov. 17, 2014 From the US Patent and Trademark Office Re. U.S. Appl. No. 13/880,066.
Restriction Official Action Dated May 24, 2018 From the US Patent and Trademark Office Re. U.S. Appl. No. 14/889,890. (8 pages).
Restriction Official Action Dated Feb. 27, 2015 From the US Patent and Trademark Office Re. U.S. Appl. No. 13/905,224.
Restriction Official Action Dated Mar. 27, 2015 From the US Patent and Trademark Office Re. U.S. Appl. No. 13/880,095.
Restriction Official Action Dated Oct. 27, 2016 From the US Patent and Trademark Office Re. U.S. Appl. No. 14/394,276.
Restriction Official Action Dated Jun. 28, 2013 From the US Patent and Trademark Office Re. U.S. Appl. No. 13/449,539.
Restriction Official Action Dated Aug. 30, 2012 From the US Patent and Trademark Office Re. U.S. Appl. No. 13/049,013.
Restriction Official Action Dated Oct. 30, 2014 From the US Patent and Trademark Office Re. U.S. Appl. No. 13/880,083.
Search Report Dated Jul. 17, 2014 From The State Intellectual Property Office of the People's Republic of China Re. Application No. 201180060741.3 and Its Machine Translation in English.
Summons to Attend Oral Proceedings Pursuant to Rule 115(1) EPC Dated Mar. 11, 2022 From the European Patent Office Re. Application No. 15862313.2. (12 Pages).
Supplemental Notice of Allowance Dated Mar. 31, 2022 from US Patent and Trademark Office Re. U.S. Appl. No. 16/494,321. (4 pages).
Supplementary European Search Report and the European Search Opinion Dated Dec. 4, 2020 From the European Patent Office Re. Application No. 18771348.2. (9 Pages).
Supplementary European Search Report and the European Search Opinion Dated Sep. 5, 2018 From the European Patent Office Re. Application No. 15862313.2. (13 Pages).
Supplementary European Search Report and the European Search Opinion Dated Dec. 22, 2016 From the European Patent Office Re. Application No. 14801877.3. (9 Pages).
Supplementary European Search Report Dated Mar. 12, 2014 From the European Patent Office Re. Application No. 11833950.6.
Translation Dated Mar. 12, 2015 of Notification of Office Action and Search Report Dated Dec. 1, 2014 From the State Intellectual Property Office of the People's Republic of China Re. Application No. 201180060862.8.
Translation Dated Nov. 18, 2015 of Notice of Reason for Rejection Dated Aug. 25, 2015 From the Japanese Patent Office Re. Application No. 2013-534435.
Ahmed et al. "Renal Sympathetic Denervation Using An Irrigated Radiofrequency Ablation Catheter for the Management of Drug-Resistant Hypertension", Journal of the American College of Cardiology: Cardiovascular Interventions, JACC, 5(7): 758-765, 2012.
Ali et al. "Signal Processing Overview of Ultrasound Systems for Medical Imaging", Texas Instruments White Paper, SPRAB12: 1-27, Nov. 2008.
Anonymus "Indication for and Results of Sympathectomy in Patients With Peripheral Vascular Disease", Lumbar Sympathectomy, Poster, 34 P., 2009.
Aoyama et al. "Comparison of Cryothermia and Radiofrequency Current in Safety and Efficacy of Catheter Ablation Within the Canine Coronary Sinus Close to the Left Circumflex Coronary Artery", Journal of Cardiovascular Electrophysiology, 16: 1218-1226, Nov. 2005.
Atherton et al. "Micro-Anatomy of the Renal Sympathetic Nervous System: A Human Postmortem Histologic Study", Clinical Anatomy, p. 1-6, Oct. 4, 2011.
Bailey et al. "Cavitation Detection During Shock-Wave Lithotripsy", Ultrasound in Medicine and Biology, XP027605630, 31(9): 1245-1256, Sep. 1, 2005. Abstract, Fig.1, p. 1246, p. 1247, r-h Col., p. 1249, r-h Col.
Baker et al. "Operative Lumbar Sympathectomy for Severe Lower Limb Ischaemia: Still a Valuable Treatment Option", Annals of the Royal College of Surgeons of England, 76(1): 50-53, Jan. 1994.
Bambi et al. "Real-Time Digital Processing of Doppler Ultrasound Signals", IEEE International Conference on Acoustics, Speech, and Signal Processing, Proceedings, (ICASSP '05), (5): v/977-v/980, Mar. 23-23, 2005.
Bandyopadhyay et al. "Outcomes of Beta-Blocker Use in Pulmonary Arterial Hypertension: A Propensity-Matched Analysis", European Respiratory Journal, 46(3): 750-760, Published Online May 28, 2015.
Bharat et al. "Monitoring Stiffness Changes in Lesions After Radiofrequency Ablation at Different Temperatures and Durations of Ablation", Ultrasound in Medicine & Biology, 31(3): 415-422, 2005.
Bhatt et al. "A Controlled Trial of Renal Denervation for Resistant Hypertension", The New England Journal of Medicine, 270(15): 1393-1401, Published Online Mar. 29, 2014.
Blankestijn et al. "Renal Denervation: Potential Impact on Hypertension in Kidney Disease?", Nephrology, Dialysis, Transplantation, 26(9): 2732-2734, Apr. 19, 2011.
Brandt et al. "Effects of Renal Sympathetic Denervation on Arterial Stiffness and Central Hemodynamics in Patients With Resistant Hypertension", Journal of the American College of Cardiology, 60(19): 1956-1965, 2012.
Brandt et al. "Renal Sympathetic Denervation Reduces Left Ventricular Hypertrophy and Improves Cardiac Function in Patients With Resistant Hypertension", Journal of the American College of Cardiology, 59(10): 901-909, 2012.
Brasselet et al. "Effect of Local Heating on Restenosis and In-Stent Neointimal Hyperplasia in the Atherosclerotic Rabbit Model: A Dose-Ranging Study", European Heart Journal, 29: 402-412, 2008.
Brinton et al. "Externally Focused Ultrasound for Sympathetic Renal Denervation", WAVE I First-In-Man Study, Kona Medical Inc., PowerPoint Presentation, TCT 2012, 15 P., 2012.
Campese et al. "Renal Afferent Denervation Prevents the Progression of Renal Disease in the Renal Ablation Model of Chronic Renal Failure in the Rat", American Journal of Kidney Diseases, 26(5): 861-865, Nov. 1995. Abstract.
Campese et al. "Sympathetic Renal Innervation and Resistant Hypertension", International Journal of Hypertension, 2011(Art.ID 814354): 1-6, 2011.
Cardiosonic "Cardiosonic New Applications", Cardiosonic, p. 1-20, Mar. 2014.

(56) References Cited

OTHER PUBLICATIONS

Cardiosonic "Histological Map of Swine Pulmonary Arteries", Cardiosonic, Animal #223, Mar. 26, 2014.
Cardiosonic "Histological Map of Swine Pulmonary Arteries", Cardiosonic, Animal #234, Mar. 18, 2014.
Cardiosonic "Histological Map of Swine Pulmonary Arteries", Cardiosonic, Animal #234, Mar. 26, 2014.
Cardiosonic "Histopathology Report", Cardiosonic, 2 P., Dec. 26, 2013.
Cardiosonic "PA/Trachea—Feedback Provisional", Cardiosonic, 5 P, Jun. 9, 2014.
Cardiosonic "PAH Preliminary Development Meeting Minutes", Cardiosonic, 2 P., Mar. 23, 2014.
Chen et al. "Artery Denervation to Treat Pulmonary Arterial Hypertension. The Single-Center, Prospective, First-in-Man PADN-1 Study (First-in-Man Pulmonary Artery Denervation for Treatment of Pulmonary Artery Hypertension)", Journal of the American College of Cardiology, JACC, 62(12): 1092-1100, Sep. 17, 2013.
Chen et al. "Hemodynamic, Functional, and Clinical Responses to Pulmonary Artery Denervation in Patients With Pulmonary Arterial Hypertension of Different Causes: Phase II Results From the Pulmonary Artery Denervation-1 Study", Circulation: Cardiovascular Interventions, 8(11): e002837-1-e002837-10, Nov. 9, 2015.
Chen et al. "Percutaneous Pulmonary Artery Denervation Completely Abolishes Experimental Pulmonary Arterial Hypertension In Vivo", EuroIntervention, 9(2): 269-276, Jun. 22, 2013.
Ciarka et al. "Prognostic Significance of Sympathetic Nervous System Activation in Pulmonary Arterial Hypertension", American Journal of Respiratory and Critical Care Medicine, 181(11): 1269-1275, Published Online Mar. 1, 2010.
CIBIS-II Investigators and Committees "The Cardiac Insufficiency Bisoprolol Study II (CIBIS-II): A Randomised Trial", The Lancet, 353(9146): 9-13, Jan. 2, 1999.
Cohn et al. "A Comparison of Enalapril With Hydralazine-Isosorbide Dinitrate in the Treatment of Chronic Congestive Heart Failure", The New England Journal of Medicine, 325(5): 303-310, Aug. 1, 1991.
Consensus Trial Study Group "Effects of Enalapril on Mortality in severe Congestive Heart Failure. Results of the Cooperative North Scandinavian Enalapril Survival Study (Consensus)", The New England Journal of Medicine, 316(23): 1429-1435, Jun. 4, 1987.
Copty et al. "Localized Heating of Biological Media Using A 1-W Microwave Near-Field Probe", IEEE Transactions on Microwave Theory and Techniques, 52(8): 1957-1963, Aug. 2004.
Copty et al. "Low-Power Near-Field Microwave Applicator for Localized Heating of Soft Matter", Applied Physics Letters, 84(25): 5109-5111, Jun. 21, 2004.
Damianou et al. "Dependence of Ultrasonic Attenuation and Absorption in Dog Soft Tissues on Temperature and Thermal Dose", Journal of the Acoustical Society of America, 102(1): 628-634, Jul. 1997.
Davies et al. "First-in-Man Safety Evaluation of Renal Denervation for Chronic Systolic Heart Failure: Primary Outcome From REACH-Pilot Study", International Journal of Cardiology, 162: 189-192, 2013.
De Man et al. "Bisoprolol Delays Progression Towards Right Heart Failure in Experimental Pulmonary Hypertension", Circulation Heart Failure, 5(1): 97-105, Published Online Dec. 9, 2011.
De Man et al. "Neurohormonal Axis in Patients With Pulmonary Arterial Hypertension. Friend or Foe?", American Journal of Respiratory and Critical Care Medicine, 187(1): 14-19, Published Online Nov. 9, 2012.
Deneke et al. "Histopathology of Intraoperatively Induced Linear Radiofrequency Ablation Lesions in Patients With Chronic Atrial Fibrillation", European Heart Journal, 26: 1797-1803, 2005.
Dewhirst et al. "Basic Principles of Thermal Dosimetry and Thermal Thresholds for Tissue Damage From Hyperthermia", International Journal of Hyperthermia, 19(3): 267-294, May-Jun. 2003.
DiBona "Neural Control of Renal Function: Cardiovascular Implications", Hypertension, 13: 539-548, 1989.
DiBona "Neural Control of the Kidney: Past, Present, and Future", Hypertension, 41: 621-624, Dec. 16, 2002.
DiBona "Physiology in Perspective: The Wisdom of the Body. Neural Control of the Kidney", American Journal of Physiology, Regulatory, Integrative and Comparative Physiology, 289(3): R633-R641, Sep. 2005.
DiBona et al. "Differentiated Sympathetic Neural Control of the Kidney", American Journal of Physiology, 271: R84-R90, 1996.
DiBona et al. "Translational Medicine: The Antihypertensive Effect of Renal Denervation", American Journal of Physiology, Regulatory, Integrative and Comparative Physiology, 298(2): R245-R253, Feb. 2010.
Diederich et al. "Catheter-Based Ultrasound Applicators for Selective Thermal Ablation: Progress Towards MRI-Guided Applications in Prostate", International Journal of Hyperthermia, 20(7): 739-756, Nov. 2004.
Diederich et al. "Catheter-Based Ultrasound Devices and MR Thermal Monitoring for Conformal Prostate Thermal Therapy", 30th Annual International IEEE EMBS Conference, Vancouver, British Columbia, Canada, Aug. 20-24, 2008, p. 3664-3668, 2008.
Diederich et al. "Induction of Hyperthermia Using An Intracavitary Multielement Ultrasonic Applicator", IEEE Transactions on Biomedical Engineering, 36(4): 432-438, Apr. 1989.
Diederich et al. "Ultrasound Technology for Hyperthermia", Ultrasound in Medicine & Biology, 25(6): 871-887, 1999.
Donoho et al. "Stable Recovery of Sparse Overcomplete Representations in the Presence of Noise", IEEE Transactions on Information Theory, 52(1): 1-42, Jan. 2006.
Drake et al. "Problematic Anatomical Sites Around the Pulmonary Artery", Gray's Anatomy for Students, 9 P., 2004.
Esler "The 2009 Carl Ludwig Lecture: Pathophysiology of the Human Sympathetic Nervous System in Cardiovascular Diseases: The Transition From Mechanisms to Medical Management", Journal of Applied Physiology, 108: 227-237, 2010.
Esler et al. "Measurement of Total and Organ-Specific Norepinephrine Kinetics in Humans", American Journal of Physiology—Endocrinology Metabolism 10, 247(1/Pt.1): E21-E28, Jul. 1984.
Esler et al. "Renal Sympathetic Denervation for Treatment of Drug-Resistant Hypertension: One-Year Results From the Symplicity HTN-2 Randomized, Controlled Trial", Circulation, 126: 2976-2982, 2012.
Failla et al. "Sympathetic Tone Restrains Arterial Distensibility of Healthy and Atherosclerotic Subjects", Journal of Hypertension, 17: 1117-1123, 1999.
Fischell PeriVascular Renal Denervation (PVRD™), Ablative Solutions Inc., TransCatheter Therapeutics Meeting, Miami, FL, USA, Oct. 24, 2012, PowerPoint Presentation, 14 P., Oct. 2012.
Fort Wayne Metals "HHS Tube", Fort Wayne Metals Research Products Corporation, 2 P., 2009.
Fujikura et al. "Effects of Ultrasonic Exposure Parameters on Myocardial Lesions Induced by High-Intensity Focused Ultrasound", Journal of Ultrasound Medicine, 25: 1375-1386, 2006.
Galie et al. "2015 ESC/ERS Guidelines for the Diagnosis and Treatment of Pulonary Hypertension. The Joint Task Force for the Diagnosis and Treatment of Pulmonary Hypertension of the European Society of Cardiology (ESC) and the European Respiratory Society (ERS). Endorsed by: Association for European Paediatric and Congenital Cardiology (AEPC), International Society for Heart and Lung Transplantation (ISHLT)", European Heart Journal, 37(1): 67-119, Published Online Aug. 29, 2015.
Galie et al. "New Treatment Stategies for Pulmonary Arterial Hypertension. Hopes or Hypes?", Journal of the American College of Cardiology, 62(12): 1101-1102, Sep. 17, 2013.
Galie et al. "Updated Treatment Algorithm of Pulmonary Arterial Hypertension", Journal of the American College of Cardiology, 62(25/Suppl.D): D60-D72, 2013.
Gander et al. "Least-Squares Fitting of Circles and Ellipses", BIT Numerical Mathematics, 34(4): 558-578, Dec. 1994.
Giering et al. "Determination of the Specific Heat Capacity of Healthy and Tumorous Human Tissue", Thermochimica Acta, 251: 199-205, Mar. 1995.

(56) References Cited

OTHER PUBLICATIONS

Glazier et al. "Laser Balloon Angioplasty Combined With Local Intrcoronary Heparin Therapy: Immediate and Short-Term Follow-Up Results", American Heart Journal, 134: 266-273, 1997.
Goswami "Renal Denervation: A Percutaneous Therapy for HTN", Prairie Heart Institute, Synvacor, The VEINS: Venous Endovascular Interventions Strategies, Chicago, USA, 42 P., 2012.
Granada et al. "A Translational Overview for the Evaluation of Peri-Renal Denervation Technologies", Cardiovascular Research Foundation, Columbai University Medical Center, New York, USA, Alizee Pathology, 25 P., 2011.
Grassi et al. "Sympathetic Mechanisms, Organ Damage, and Antihypertensive Treatment", Current Hypertension Report, 13: 303-308, 2011.
Griffiths et al. "Thoraco-Lumbar Splanchnicectomy and Sympathectomy. Anaesthetic Procedure", Anaesthesia, 3(4): 134-146, Oct. 1948.
Grimson et al. "Total Thoracic and Partial to Total Lumbar Sympathectomy, Splanchnicectomy and Celiac Ganglionectomy for Hypertension", Annals of Surgery, 138(4): 532-547, Oct. 1953.
Heath et al. "The Structure of the Pulmonary Trunk at Different Ages and in Cases of Pulmonary Hypertension and Pulmonary Stenosis", The Journal of Pathology and Bacteriology, 77(2): 443-456, Apr. 1959.
Hering et al. "Renal Denervation in Moderate to Severe CKD", Journal of the American Society of Nephrology, 23: 1250-1257, 2012.
Hering et al. "Substantial Reduction in Single Sympathetic Nerve Firing After Renal Denervation in Patients With rRsistant Hypertension", Hypertension, 61: 1-14, Nov. 19, 2012.
Holdaas et al. "Modulation of Reflex Renal Vasoconstriction by Increased Endogenous Renal Prostaglandin Synthesis", The Journal of Pharmacology and Experimental Therapeutics, 232(3): 725-731, 1985.
Humbert et al. "Advances in Therapeutic Interventions for Patients With Pulmonary Arterial Hypertension", Circulation, XP055531396, 130(24): 2189-2208, Published Online Dec. 9, 2014.
Janssen et al. "Role of Afferent Renal Nerves in Spontaneous Hypertension in Rats", Hypertension, 13: 327-333, 1989.
Joner "Histopathological Characterization of Renal Arteries After Radiofrequency Catheter Based Sympathetic Denervation in a Healthy Porcine Model", Deutsches Herzzentrum M?nchen, Technische Universit?t M?nchen, PowerPoint Presentation, TCT 2012, 15 P., 2012.
Katholi "Renal Nerves in the Pathogenesis of Hypertension in Experimental Animals and Humans", American Journal of Physiology, 245: F1-F14, 1983.
Katholi et al. "Intrarenal Adenosine Produces Hypertension by Activating the Sympathetic Nervous System Via the Renal Nerves in the Dog", Journal of Hypertension, 2: 349-359, 1984.
Katholi et al. "Renal Nerves in the Maintenance of Hypertension: A Potential Therapeutic Target", Current Hypertension Reports, 12(3): 196-204, Jun. 2010.
Kleinlogel et al. "A Gene-Fusion Strategy for Stoichiometric and Co-Localized Expression of Light-Gated Membrane Proteins", Nature Methods, 8(12): 1083-1091, Dec. 2011.
Kline et al. "Functional Reinnervation and Development of Supersensitivity to NE After Renal Denervation in Rats", American Journal of Physiology, 238: R353-R358, 1980.
Kolh "Carotid Denervation by Adventitial Stripping: A Promising Treatment of Carotid Sinus Syndrome?", European Journal of Vascular and Endovascular Surgery, 39(2): 153-154, Feb. 2010.
Krum et al. "Catheter-Based Renal Sympathetic Denervation for Resistant Hypertension: A Multicentre Safety and Proof-of-Principle Cohort Study", The Lancet, 373: 1275-1281, Apr. 11, 2009.
Krum et al. "Catheter-Based Renal Sympathetic Denervation for Resistant Hypertension: A Multicentre Safety and Proof-of-Principle Cohort Study", The Lancet, 373: 1275-1281, Mar. 30, 2009.
Kummer "Pulmonary Vascular Innervation and Its Role in Responses to Hypoxia: Size Matters!", Proceedings of the American Thoracic Society, 8(6): 471-476, Nov. 1, 2011.
Lafon "Miniature Devices for Minimally Invasive Thermal Ablation by High Intensity Ultrasound", Cargese Workshop 2009, University of Lyon, France, INSERM U556, Presentation, 39 P., 2009.
Lambert et al. "Redo of Percutaneous Renal Denervation in a Patient With Recurrent Resistant Hypertension After Primary Treatment Success", Catheterization and Cardiovascular Interventions, p. 1-11, 2012.
Lele "Effects of Focused Ultrasonic Radiation on Peripheral Nerve, With Observations on Local Heating", Experimental Neurology, 8: 47-83, 1963.
Lemoine et al. "Amputations and Sympathectomy in Peripheral Vascular Disease of the Lower Extremity. Experience With 180 Patients", Journal of the National Medical Association, 61(3): 219-221, May 1969.
Li et al. "Acoustic Proximity Ranging in the Presence of Secondary Echoes", IEEE Transactions on Instrumentation and Measurement, XP011102759, 52(5): 1593- 1605, Oct. 1, 2003. p. 1593.
Lin et al. "Utility of the PlasmaKinetic™ Bipolar Forceps® for Control of the Renal Artery in a Porcine Model", JTUA, 14(3): 118-121, Sep. 2003.
Liu et al. "A Helical Microwave Antenna for Welding Plaque During Balloon Angioplasty", IEEE Transactions on Microwave Theory and Techniques, 44(10): 1819-1831, Oct. 1996.
Liu et al. "Pulmonary Artery Denervation Improves Pulmonary Arterial Hypertension Induced Right Ventricular Dysfunction by Modulating the Local Renin-Angiotensin-Aldosterone System", BMC Cardiovascular Disorders, 16(1): 192-1-192-10, Oct. 10, 2016.
Lopez et al. "Effects of Sympathetic Nerves on Collateral Vessels in the Limb of Atherosclerosis Primates", Atherosclerosis, 90: 183-188, 1991.
Mabin et al. "First Experience With Endovascular Ultrasound Renal Denervation for the Treatment of Resistant Hypertension", EuroIntervention, 8: 57-61, 2012.
Mahfoud et al. "Effect of Renal Sympathetic Denervation on Glucose Metabolism in Patients With Resistant Hypertension: A Pilot Study", Circulation, 123: 1940-1946, 2011.
Mahfoud et al. "Is There a Role for Renal Sympathetic Denervation in the Future Treatment of Resistant Hypertension?", Future Cardiology, 7(5): 591-594, 2011.
Mahfoud et al. "Renal Hemodynamics and Renal Function After Catheter-Based Renal Sympathetic Denervation in Patients With Resistant Hypertension", Hypertension, 60: 419-424, 2012.
Makris et al. "Resistant Hypertension Workup and Approach to Treatment", International Journal of Hypertension, 2011: 1-10, 2011.
Manasse et al. "Clinical Histopathology and Ultrstructural Analysis of Myocardium Following Microwave Energy Ablation", European Journal of Cardio-Thoracic Surgery, 23: 573-577, 2003.
Mangoni et al. "Effect of Sympathectomy on Mechanical Properties of Common Carotid and Femoral Arteries", Hypertension, 30: 1085-1088, 1997.
Martin et al. "Premise, Promise, and Potential Limitations of Invasive Devices to Treat Hypertension", Current Cardiology Reports, 13(1): 86-92, Feb. 2011.
Mazor "Efficacy of Renal Denervation Is Positively Impacted by Longitudinal Treatments", Vessix Vascular Inc., PowerPoint Presentation, TCT 2012, 20 P., 2012.
MERIT-HF Study Group "Effect of Metaprolol CR/XL in Chronic Heart Failure: Metoprolol CR/XL Randomised Intervention Trial in Congestive Heart Failure (MERIT-HF)", The Lancet, 353(9169): 2001-2007, Jun. 12, 1999.
Mogil et al. "Renal Innervation and Renin Activity in Salt Metabolism and Hypertension", American Journal of Physiology, 216(4): 693-697, Apr. 1969.
Moretti et al. "Beta Blocker for Patients With Pulmonary Arterial Hypertension: A Single Center Experience", International Journal of Cardiology, 184(1): 528-532, Available Online Feb. 24, 2015.

(56) References Cited

OTHER PUBLICATIONS

Mortensen et al. "Catheter-Based Renal Sympathetic Denervation Improves Central Hemodynamics and Arterial Stiffness: A Pilot Study", The Journal of Clinical Hypertension, 14(12): 861-870, Dec. 2012.
Nootens et al. "Neurohormonal Activation in Patients With Right Ventricular Failure From Pulmonary Hypertension: Relation to Hemodynamic Variables and Endothelin Levels", Journal of the American College of Cardiology, JACC, 26(7): 1581-1585, Dec. 1995.
Ohkubo et al. "Histological Findings After Angioplasty Using Conventional Balloon, Radiofrequency Thermal Balloon, and Stent for Experimental Aortic Coarctation", Pediatrics International, 46: 39-47, 2004.
Olafsson et al. "Ultrasound Current Source Density Imaging", IEEE Transactions on Biomedical Engineering, 55(7): 1840-1848, Jul. 2008.
Ong et al. "Successful Treatment of Resistant Hypertension With Percutaneous Renal Denervation Therapy", Heart, 98(23): 1754-1755, Dec. 2012.
Ormiston "OneShot (Covidien)", Maya Medical, Auckland, New Zealand, PowerPoint Presentation.
Ormiston et al. "First-in-Human Use of the OneShot™ Renal Denervation System From Covidien", EuroIntervention, 8: 1090-1094, 2013.
Packer et al. "Effect of Carvedilol on Survival in Severe Chronic Heart Failure", The New England Journal of Medicine, 344(22): 1651-1658, May 31, 2001.
Page et al. "The Effect of Renal Denervation on Patients Suffering From Nephritis", The Journal of Clinical Investigation, 14(4): 443-458, Jul. 1935.
Papademetriou et al. "Renal Sympathetic Denervation for the Treatment of Difficult-to-Control or Resistant Hypertension", International Journal of Hypertension, 2011: 1-8, Jan. 2011.
Para Tech Coating "Parylene Properties", Para Tech Coating Inc., 1 P., 2010.
Perros et al. "Nebivolol for Improving Endothelial Dysfunction, Pulmonary Vascular Remodeling, and Right Heart Function in Pulmonary Hypertension", Journal of the American College of Cardiology, JACC, 65(7): 668-680, Feb. 24, 2015.
Pokushalov et al. "A Randomized Comparison of Pulmonary Vein Isolation With Versus Without Concomitant Renal Artery Denervation in Patients With Refractory Symptomatic Atrial Fibrillation and Resistant Hypertension", Journal of the American College of Cardiology, 60(13): 1163-1170, 2012.
Prapa et al. "Histopathology of the Great Vessels in Patients With Pulmonary Arterial Hypertension in Association With Congenital Heart Disease: Large Pulmonary Arteries Matter Too", international Journal of Cardiology, 168: 2248-2254, Available Online Feb. 28, 2013.
Prochnau et al. "Catheter-Based Renal Denervation for Drug-Resistant Hypertension by Using a Standard Electrophysiology Catheter", EuroIntervention, 7: 1077-1080, 2012.
Prochnau et al. "Efficacy of Renal Denervation With a Standard EP Catheter in the 24-h Ambulatory Blood Pressure Monitoring—Long-Term Follow-Up", International Journal of Cardiology, 157(3): 447-448, Jun. 14, 2012.
Qin "Physician's Prescription Manual", Wen-han, Qin: 590, People's Military Medical Press, Feb. 1998 with Machine Translation.
Quinn "Pre-Eclampsia and Partial Uterine Denervation", Medical Hypotheses, 64(3): 449-454, 2005. Abstract.
Rappaport "Treating Cardiac Disease With Catheter-Based Tissue Heating", IEEE Microwave Magazine, p. 57-64, Mar. 2002.
Reddy "Sound Intervention", Mount Sinai School of Medicine, MSSM, Presentation, 19 P., 2012.
Roehl et al. "Comparison of 3 Methods to Induce Acute Pulmonary Hypertension in Pigs", Comparative Medicine, 59(3): 280-286, Jun. 2009.
Rosanio et al. "Pulmonary Arterial Hypertension in Adults: Novel Drugs and Catheter Ablation Techniques Show Promise? Systematic Review on Pharmacotherapy and Interventional Strategies", BioMed Research International, XP055754039, 2014: 1-17, Jun. 12, 2014.
Rothman "FIM Evaluation of a New, Multi-Electrode RF System for Renal Denervation (Medtronic)", Medtronic Inc., PowerPoint Presentation, 8 P., 2012.
Rothman et al. "Pulmonary Artery Denervation Reduces Pulmonary Artery Pressure and Induces Histological Changes in An Acute Porcine Model of Pulmonary Hypertension", Circulation: Cardiovascular Interventions, 8(11): e002569-1-e002569-7, Published Online Nov. 17, 2015.
Rousselle "Experimental Pathways for the Evaluation of Extrinsic Renal Nerve Distribution, Density, and Quantification (Swine Model)", Alizee Pathology in Collaboration With Jack Skirkball Center for Cardiovascular Research, TCT, 20 P., Nov. 8, 2011.
Rousselle "Renal Artery Dervation: Experimental Pathways for the Evaluation of Extrinsic Renal Nerve Distribution, Density, and Quantification (Swine Model)", Alizee Pathology, Cardiovascular Research Foundation, Nov. 8, 2011.
Sakakura et al. "Methodological Standardization for the Pre-Clinical Evaluation of Renal Sympathetic Denervation", JACC: Cardiovascular Interventions. 7(10): 1184-1193, Published Online Sep. 14, 2014.
Sangiorgi et al. "Histo-Morphometric Evaluation of 2D Characteristics and 3D Sympatetic Renal Nerve Distribution in Hypertensive Vs. Normotensive Patients", Department of Pathology, Department of Cardiology, University of Rome Tor Vergata, Department of Cardiology University of Modena and Reggio Emilia, Medtronic Cardiovascular, PowerPoint Presentation, TCT 2012, 22 P., 2012.
Sanni et al. "Is Sympathectomy of Benefit in Critical Leg Ischaemia Not Amenable to Revascularisation?", Interactive Cardio Vascular and Thoracic Surgery, 4: 478-483, 2005.
Scheinert "Cardiosonic TIVUS• Technology: An Intra-Vascular Ultrasonic Catheter for Targeted Renal Denervation", Center for Vascular Medicine, Park Hospital Leipzig, Germany, PowerPoint Presentation, TCT 2012, 16 P., 2012.
Schelegle et al. "Vagal Afferents Contribute to Exacerbates Airway Responses Following Ozone and Allergen Challenge", Respiratory Physiology & Neurobiology, 181(3): 277-285, May 31, 2012.
Schlaich "Long-Term Follow Up of Catheter-Based Renal Denervation for Resistant Hypertension Confirms Durable Blood Pressure Reduction", Hypertension & Kidney Disease Laboratory, Baker IDI Heart & Diabetes Institute, Melbourne VIC, Australia, PowerPoint Presentation, TCT 2012, 22 P., 2012.
Schlaich et al. "Renal Sympathetic-Nerve Ablation for Uncontrolled Hypertension", New England Journal of Medicine, 361(9): 932-934, Aug. 27, 2009.
Schnyder et al. "Common Femoral Artery Anatomy Is Influenced by Demographics and Comorbidity: Implications for Cardiac and Peripherial Invasive Studies", Catheterization and Cardiovascular Interventions, 53(3): 289-295, Jul. 2001.
Schwartz "Strategies to Model Efficacy of Hypertension Devices", EuroPCR 2013, The Leading Cardiovascular Course, 24 P., 2013.
Shelton Jr. et al. "A Nondestructive Technique to Measure Pulmonary Artery Diameter and Its Pulsatile Variations", Journal of Applied Physiology, 33(4): 542-544, Oct. 1972.
Shung "Doppler Flow Measurements", Diagnostic Ultrasound—Imaging and Blood Flow Measurements, Chap.5:103-104, 2006.
Sievert et al. "Catheter-Based Technology Alternatives for Renal Denervation", Cardio Vascular Center Frankfurt, Germany, TCT 2012, Miami, FL, USA, Oct. 22-26, 2012, PowerPoint Presentation, 35 P., Oct. 2012.
Simonneau et al. "Updated Clinical Classification of Pulmonary Hypertension", Journal of the American College of Cardiology, 54(1/Suppl.S): S43-S54, Jun. 30, 2009.
Sitbon et al. "Beyond a Single Pathway: Combination Therapy in Pulmonary Arterial Hypertension", European Respiratory Review, 25(142): 408-417, Dec. 2016.
SOLVD Investigators "Effect of Enalapril on Survival in Patients With Reduced Left Ventricular Ejection Fractions and Congestive Heart Failure", The New England Journal of Medicine, 325(5): 293-302, Aug. 1, 1991.

(56) References Cited

OTHER PUBLICATIONS

Souchon et al. "Monitoring the Formation of Thermal Lesions With Heat-Induced Echo-Strain Imaging: A Feasibility Study", Ultrasound in Medicine & Biology, 31(2): 251-259, 2005.
Stefanadis "Vincristine Local Delivery for Renal Artery Denervation", Athens, Greece, PowerPoint Presentation, TCT 2012, 21 P., 2012.
Steigerwald et al. "Morphological Assessment of Renal Arteries After Radiofrequency Catheter-Based Sympathetic Denervation in a Porcine Model", Journal of Hypertension, 30(11): 2230-2239, Nov. 2012.
Swierblewska et al. "An Independent Relationship Between Muscle Sympathetic Nerve Activity and Pulse Wave Velocity in Normal Humans", Journal of Hypertension, 28: 979-984, 2010.
Symplicity HTN-1 Investigators "Catheter-Based Renal Sympathetic Denervation for Resistant Hypertension: Durability of Blood Pressure Reduction Out to 24 Months", Hypertension, 57: 911-917, Mar. 14, 2011.
Symplicity HTN-2 Investigators "Renal Sympathetic Denervation in Patients With Treatment-Resistant Hypertension (The Symplicity HTN-2 Trial): A Randomised Controlled Trial", The Lancet, 376(9756): 1903-1909, Published Online Nov. 17, 2010.
Symplicity HTN-2 Investigators "Renal Sympathetic Denervation in Patients With Treatment-Resistant Hypertension (The Symplicity HTN-2 Trial): A Randomised Controlled Trial", The Lancet, 376: 1903-1909, Dec. 4, 2010.
Szabo "Diagnostic Ultrasound Imaging Inside Out", Academic Press Series in Biomedical Engineering, 2004.
Techavipoo et al. "Temperature Dependence of Ultrasonic Propagation Speed and Attenuation in Excised Canine Liver Tissue Measured Using Transmitted and Reflected Pulses", Journal of the Acoustical Society of America, 115(6): 2859-2865, Jun. 2004.
Thenappan et al. "Beta-Blocker Therapy Is Not Associated With Adverse Outcomes in Patients With Pulmonary Arterial Hypertension. A Propensity Score Analysis", Circulation Heart Failure, 7(6): 903-910, Published Online Oct. 2, 2014.
Tibshirani "Regression Shrinkage and Selction Via the Lasso: A Retrospective", Journal of the Royal Statistical Society, Series B: Statistical Methodology, 73(Pt.3): 273-282, 2011.
Tibshirani "Regression Shrinkage and Selection Via the Lasso", Journal of the Royal Statistical Society, Series B: Methodological, 58(1): 267-288, 1996.
Toorop et al. "Clinical Results of Carotid Denervation by Adventitial Stripping in Caotid Sinus Syndrome", Europan Journal of Vascular and Endovascular Syndrome, 39: 146-152, 2010.
Tyreus et al. "Two-Dimensional Acoustic Attenuation Mapping of High-Temperature Interstitial Ultrasound Lesions", Physics in Medicine and Biology, 49: 533-546, 2004.
Van Albada et al. "Biological Serum Markers in the Managment of Pediatric Pulmonary Arterial Hypertension", Pediatric Research, 63(3): 321-327, Mar. 2008.
Van Campen et al. "Bisoprolol in Idiopathic Pulmonary Arterial Hypertension: an Explorative Study", European Respiratory Journal, 48: 787-796, 2016.
Velez-Roa et al. "Increased Sympathetic Nerve Activity in Pulmonary Artery Hypertension", Circulation, 110(10): 1308-1312, Sep. 7, 2004.
Verloop et al. "The Effects of Renal Denervation on Renal Haemodynamics", Interventions for Hypertenison & Heart Failure, Abstracts of EuroPCR & AsiaPCR/SingLIVE 2013, May 21, 2013.
Virmani "Translation Medicine and Renal Denervation: Pre-Clinical Animal Models and Histoanatomy", CVPath Institute, Gaithersburg, MD, USA, PowerPoint Presentation.
Voskuil et al. "Percutaneous Renal Denervation for the Treatment of Resistant Essential Hypertension; The First Dutch Experience", Netherlands Heart Journal, 19(7-8): 319-323, Aug. 2011.
Warwick et al. "Trackless Lesions in Nervous Tissues Produced by High Intensity Focused Ultrsound (High-Frequency Mechanical Waves)", Journal of Anatomy, 102(3): 387-405, 1968.

Wei-Feng "New Theories and New Technologies for Cardiovascular Diseases", People's Military Medical Press, 324: 3P., 2015. ( Chinese only).
Wikswo Jr. et al. "Magnetic Field of a Nerve Impulse: First Measurements", Science, 208: 53-55, Apr. 4, 1980.
Wilcox "Resistant Hypertension and the Role of the Sympathetic Nervous System", Medtronic, 30 P.
Williams et al. "Laser Energy Source in Surgical Atrial Fibrillation Ablation: Preclinical Experience", The Annals of Thoracic Surgery, 82: 2260-2264, 2006.
Witkowski "Future Perspective in Renal Denervation: Congestive Heart Failure, Insulin Resistance and Sleep Apnea", Innovations in Cardiovascular Interventions, ICI Meeting 2011, Tel Aviv, Israel, Dec. 4-6, 2011, 23 P., 2011.
Witkowski et al. "Effects of Renal Sympathetic Denervation on Blood Pressure, Sleep Apnea Course, and Glycemic Control in Patients With Resistant Hypertension and Sleep Apnea", Hypertension, 58(4): 559-565, Oct. 2011.
Witkowski et al. "Effects of Renal Sympathetic Denervation on Blood Pressure, Sleep Apnea Course, and Glycemic Control in Patients With Resistant Hypertension and Sleep Apnea", Hypertension, 58: 559-565, Aug. 15, 2011.
Witte et al. "Imaging Current Flow in Lobster Nerve Cord Using the Acoustoelectric Effect", Applied Physics Letters, 90: 163902-1-163902-3, 2007.
Wolf-De Jonge et al. "25 Years of Laser Assisted Vascular Anastomosis (LAVA): What Have We Learned?", European Journal of Vascular and Endovascular Surgery, 27(5): 466-476, May 2004.
Worthington et al. "Changes in Ultrasound Properties of Porcine Kidney Tissue During Heating", Ultrasound in Medicine & Biology, 27(5): 673-682, 2001.
Worthington et al. "Ultrasound Properties of Human Prostate Tissue During Heating", Ultrsound in Medicine & Biology, 28(10): 1311-1318, 2002.
Wright "On a Relationship Between the Arrhenius Parameters From Thermal Damage Studies", Transactions of the ASME, Technical Brief, Journal of Biomechanical Engineering, 125(2): 300-304, Apr. 9, 2003.
Wu et al. "A Quality Control Program for MR-Guided Focused Ultrasound Ablation Therapy", Journal of Applied Clinical Medical Physics, 3(2): 162-167, Spring 2002.
Wu et al. "Noninvasive Cardiac Arrhythmia Therapy Using High-Intensity Focused Ultrasound (HIFU) Ablation", International Journal of Cardiology, 166(2): e28-e30, Available Online Feb. 26, 2013.
Xu et al. "Experimental Nerve Thermal Injury", Brain, 117: 375-384, 1994.
Zeller "Percutaneous Renal Denervation System. The New Ultrasound Solution for the Mangament of Hypertension", Paradise Ultrasound Denervation System, ReCor Medical, 27 P., 2013.
Zhang et al. "Pulmonary Arterial Hypertension: Pharmacologic Therapies and Potential Pulmonary Artery Denervation Treatment", EuroIntervention, XP009524288, 9(Suppl.R): R149-R154, May 2013.
Zhou et al. "Pulmonary Artery Denervation Attenuates Pulmonary Arterial Remodeling in Dogs With Pulmonary Arterial Hypertension Induced by Dehydrogenized Monocrotaline", JACC: Cardiovascular Interventions, 8(15): 2013-2023, Dec. 28, 2015.
Restriction Official Action Dated Dec. 14, 2022 from the US Patent and Trademark Office Re. U.S. Appl. No. 17/187,813. (8 pages).
Interview Summary Dated May 1, 2024 from the US Patent and Trademark Office Re. U.S. Appl. No. 16/494,322. (2 pages).
Interview Summary Dated Jun. 5, 2023 from the US Patent and Trademark Office Re. U.S. Appl. No. 16/540,191. (3 pages).
Notice of Allowance Dated Apr. 3, 2023 from US Patent and Trademark Office Re. U.S. Appl. No. 16/451,087. (9 pages).
Official Action Dated Apr. 3, 2023 from the US Patent and Trademark Office Re. U.S. Appl. No. 17/187,813. (55 pages).
Official Action Dated Mar. 7, 2024 from the US Patent and Trademark Office Re. U.S. Appl. No. 17/719,412. (57 pages).
Official Action Dated Nov. 14, 2023 from the US Patent and Trademark Office Re. U.S. Appl. No. 17/187,813. (15 pages).
Official Action Dated Jan. 24, 2024 From the US Patent and Trademark Office Re. U.S. Appl. No. 16/439,816. (16 Pages).

(56) References Cited

OTHER PUBLICATIONS

Official Action Dated May 24, 2023 from the US Patent and Trademark Office Re. U.S. Appl. No. 16/494,322. (113 pages).
Official Action Dated Apr. 25, 2024 from the US Patent and Trademark Office Re. U.S. Appl. No. 18/235,904. (46 pages).
Official Action Dated Jan. 26, 2024 from the US Patent and Trademark Office Re. U.S. Appl. No. 16/540,191. (20 pages).
Official Action Dated Jun. 26, 2023 from the US Patent and Trademark Office Re. U.S. Appl. No. 16/439,816. (59 pages).
Restriction Official Action Dated Aug. 1, 2023 from the US Patent and Trademark Office Re. U.S. Appl. No. 17/719,412. (8 pages).
Interview Summary Dated Jul. 26, 2024 from the US Patent and Trademark Office Re. U.S. Appl. No. 16/540,191. (8 pages).

\* cited by examiner

METHOD AND/OR APPARATUS FOR MEASURING RENAL DENERVATION EFFECTIVENESS

RELATED APPLICATION

This application is a Division of U.S. patent application Ser. No. 13/905,224 filed on May 30, 2013 which claims the benefit of priority under 35 USC § 119(e) of U.S. Provisional Patent Application No. 61/653,515 filed on May 31, 2012, the contents of which are incorporated herein by reference in their entirety.

FIELD AND BACKGROUND OF THE INVENTION

The present invention, in some embodiments thereof, relates to methods and/or apparatuses for measuring the effectiveness of a renal denervation treatment. A renal denervation is a procedure aimed at treating refractory hypertension, also considered as uncontrollable high blood pressure. Renal denervation uses ablation to reduce the activity of renal artery nerves. By reducing the sympathetic neural activity, blood pressure may be reduced.

European publication number 2594193 to Fain et al. discloses: "A renal denervation feedback method is described that performs a baseline measurement of renal nerve plexus electrical activity at a renal vessel; denervates at least some tissue proximate the renal vessel after performing the baseline measurement; performs a post-denervation measurement of renal nerve plexus electrical activity at the renal vessel, after the denervating; and assesses denervation of the renal vessel based on a comparison of the baseline measurement and the post-denervation measurement of renal nerve plexus electrical activity at the renal vessel."

SUMMARY OF THE INVENTION

According to an aspect of some embodiments of the invention, there is provided a method for assessing renal denervation treatment, comprising inserting a measurement device into an artery, tracking at least one of arterial wall movement, arterial blood flow rate, arterial blood flow velocity, blood pressure and arterial diameter at one or more selected locations in the renal artery over time, and assessing the effectiveness of the renal denervation treatment according to results obtained by the tracking. In some embodiments, the selected location is a location of tissue ablation. In some embodiments, the selected location is at a distance of at least 0.5 cm from a location of tissue ablation. In some embodiments, tracking over time comprises measuring at least one of the parameters continuously during the denervation treatment. In some embodiments, tracking over time comprises measuring at least one of the parameters periodically every 30 seconds. In some embodiments, assessing is performed by analyzing measurement results of two or more parameters combined together. In some embodiments, assessing comprises detecting a change in arterial diameter over time. In some embodiments, a stiffness of the artery is determined according to an arterial wall movement profile measured over time. In some embodiments, effectiveness is assessed by comparing pre-denervation and post-denervation measurements. In some embodiments, a single measurement device adapted for emitting and receiving ultrasonic energy is used for treating and for measuring. In some embodiments, the measurement device is positioned externally to the renal artery. In some embodiments, a denervation treatment profile is adjusted according to results of the tracking of at least one parameter. In some embodiments, assessing comprises determining if the denervation treatment should be repeated by applying a threshold to the at least one tracked parameter. Optionally, adjusting the denervation treatment profile comprises selecting at least one of a treatment duration, a treatment location, and an intensity of the applied energy for denervating the nerves.

According to an aspect of some embodiments of the invention, there is provided a device comprising a plurality of ultrasonic transceivers for determining effectiveness of a renal denervation treatment, wherein the device is adapted to measure renal artery stiffness using ultrasonic imaging. In some embodiments, the device is adapted to measure renal artery wall movement using echo signals reflected by the artery wall. In some embodiments, the device is adapted to calculate an amplitude of the artery wall movement by measuring a distance between at least one of the transceivers and the artery wall. In some embodiments, the device is adapted to measure a diameter of the renal artery using ultrasonic imaging. In some embodiments, the device is adapted to measure renal artery stiffness by calculating pulse wave velocity.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

Figure 1:
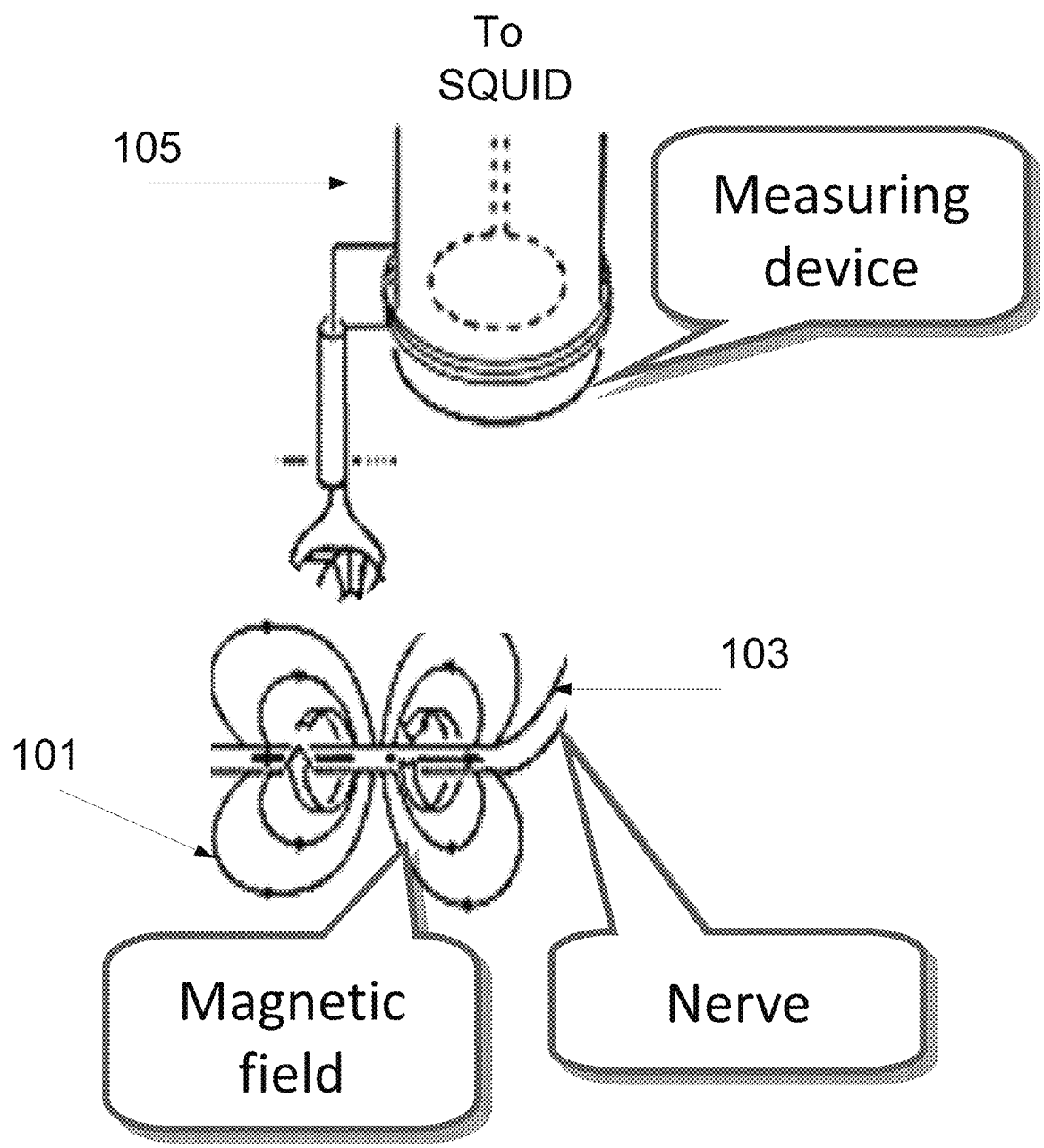
FIG. 1 is a schematic illustration of a method for measuring a magnetic field induced by neural activity, according to some embodiment of the invention.

The present invention, in some embodiments thereof, relates to methods and/or apparatuses for measuring the effectiveness of a renal denervation treatment.

A broad aspect of some embodiments of the invention relates to obtaining feedback following a renal denervation treatment by measuring physiological parameters of the blood vessel and/or parameters relating to blood flow and/or parameters relating to neural activity and/or measuring a response to stimulation.

An aspect of some embodiments relates to measuring physiological changes over time at one or more selected locations along the renal artery. In some embodiments, the method comprises measuring physiological changes related to mechanical properties of the artery, such as blood flow rate, blood pressure, blood flow velocity, arterial diameter and/or artery wall movement. In some embodiments, measurements are performed at a tissue ablation location. Additionally and/or alternatively, measurements are performed at a location in some distance from the tissue ablation location, for example at a distance of 2 cm, 0.5 cm, 4 cm or intermediate, larger or smaller distances from the denervation location, for example in vertical and/or horizontal directions in the artery.

In some embodiments, measurements are performed before and/or during and/or after denervation treatment. In some embodiments, measurements are performed periodically during the treatment, for example every second, every 2 minutes, every 15 minutes, or intermediate, shorter or longer time intervals. Optionally, the intervals are fixed intervals. Alternatively, the intervals vary, for example the intervals may be adjusted according to parameters such as the treatment duration at each of the locations in the artery. Optionally, measurements are performed continuously. In some embodiments, the duration of the treatment is, for example, between 0.5-4 hours, and measurements are performed at specific time points during the treatment.

In some embodiments, an arterial wall movement pattern is detected. In some embodiments, a narrowing and/or widening of the renal artery is detected. Optionally, arterial stiffness is assessed. Optionally, potential kidney functioning is assessed. In some embodiments, kidney function is determined according to arterial stiffness.

In some embodiments, a pattern may include a repetitive behavior, trend, and/or any other detected behavior of, for example, arterial diameter, arterial wall movement, blood pressure, and/or any other parameters described herein. Optionally, the pattern is detected over time. In one example, an arterial diameter pattern may include a repetitive behavior, for example narrowing and widening of the artery diameter in fixed time intervals, which may be linked to and/or indicate pulsation.

In some embodiments, the measured data is analyzed to deduce the effectiveness of the denervation treatment. In some embodiments, a threshold may be applied to determine if the treatment profile should be adjusted and/or to determine if the treatment should be repeated. In some embodiments, the results of at least two measured parameters, for example arterial diameter and blood flow velocity, are combined to deduce effectiveness.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

An Exemplary Method for Measuring 1 Magnetic Field Induced by Neural Activity

Referring now to the drawings, FIG. 1 describes a method for measuring the magnetic field 101 inside a blood vessel lumen, according to some embodiment of the invention. Optionally, the magnetic field reflects a total magnetic field induced by current in the nerves 103 surrounding the blood vessel. In some embodiments, a SQUID magnetometer 105 comprising one or more coils is used for measuring the magnetic field. Optionally, a plurality of coils are arranged in a parallel and/or serial manner and/or combination of them. Optionally, neural activity is stimulated, for example using an electrode within the artery, to initiate current in the nerves, and a SQUID magnetometer or any other magnetic field detecting device is used for measuring the magnetic field induced by the current conducted through the nerves. Optionally, a magnetic field within a lumen of the artery and/or a magnetic field externally to the artery is measured. Optionally, a stimulating device such as an electrode is positioned outside the artery. Optionally, a sensor for detecting the magnetic field is positioned outside the artery.

An Exemplary Method for Evaluating and/or Measuring Renal Denervation by Detecting Current Source Density of Renal Neural Signals Using Ultrasound Current Source Density Imaging (UCSDI)

Figure 2:
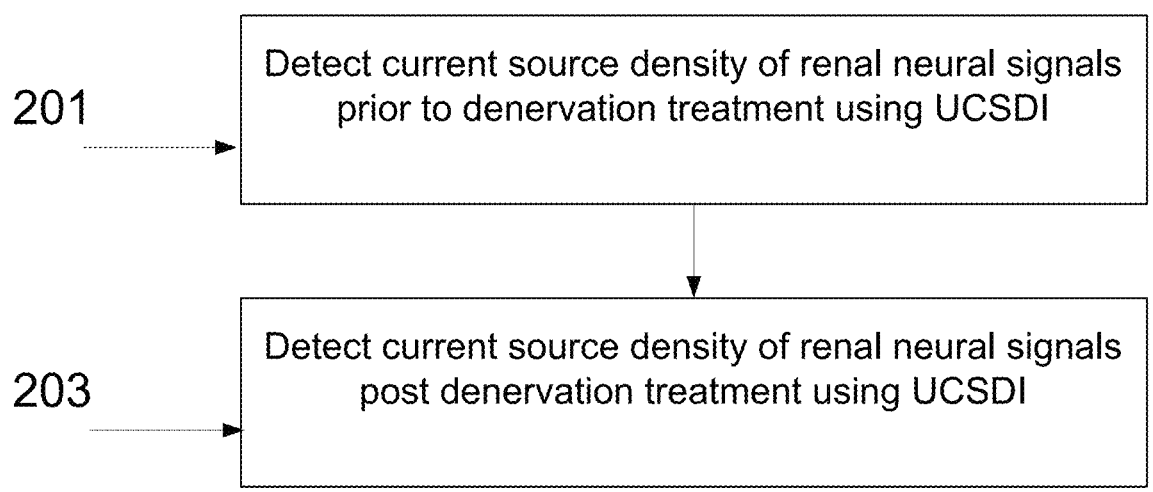
FIG. 2 is a flowchart of a method for evaluating and/or measuring renal denervation by detecting current source density of renal neural signals using ultrasound current source density imaging (UCSDI), according to some embodiments of the invention.

FIG. 2 is a flowchart of a method for evaluating and/or measuring renal denervation by detecting current source density of renal neural signals using ultrasound current source density imaging (UCSDI), according to some embodiments of the invention. In some embodiments, the current source density is detected, for example distally to the denervation location, before (201) and/or after a renal denervation procedure (203). The technique is a direct 3-D imaging technique that potentially facilitates existing mapping procedures with superior spatial resolution. The technique is based on a pressure induced change in resistivity—acousto-electric (AE) effect, which is spatially confined to the ultrasound focus. Optionally, AE modulated voltage recordings are used to map and reconstruct the current densities. In some embodiments, a device such as a catheter comprising one or more ultrasonic transceivers and/or transducers is inserted into the renal artery. Optionally, ultrasonic energy is emitted by the device, and returning echo signals are received and/or recorded for further analysis.

Figure 3A:
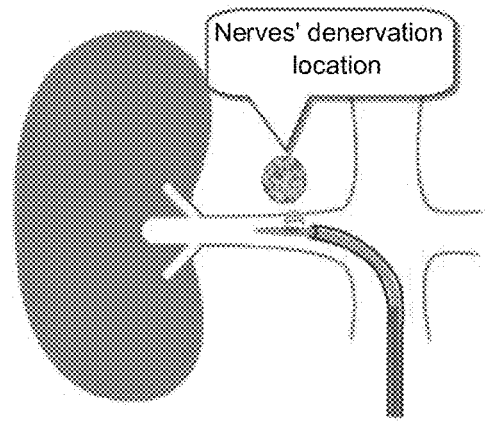
FIGS. 3A-3C are schematic illustrations and a flowchart of methods that include initiating an electric impulse to the artery wall, according to some embodiments of the invention.
Figure 3B:
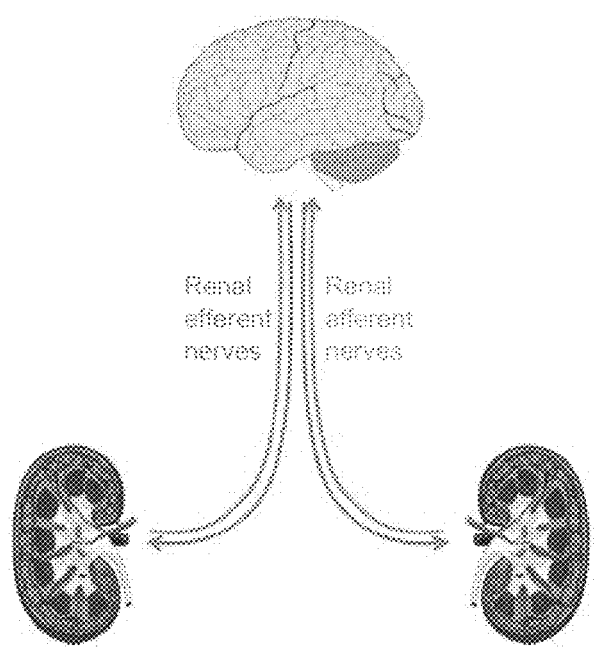
Figure 3C:
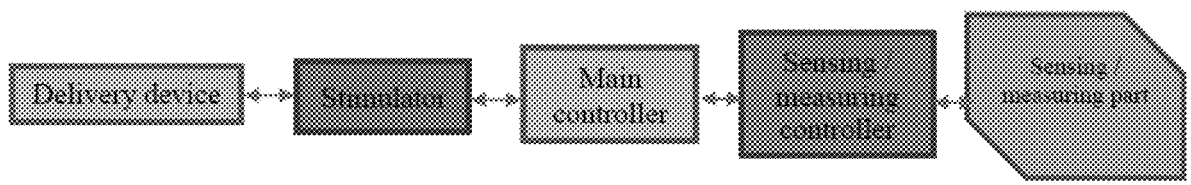

Exemplary Methods for Denervation Assessment which Include Initiation of an Electric Impulse to the Artery Wall FIGS. 3A-3C relate to methods that include initiating an electric impulse to the artery wall, according to some embodiments of the invention. The following procedures may be performed:

1. Initiate an electric impulse to the artery wall, proximally to the denervation location, in order to stimulate the nerve and trigger an action potential in the nerves surrounding the artery wall, and measure the magnetic field at the distal location from the denervation position (FIG. 3A), for example using a SQUID magnetometer.

2. Initiate an electric impulse to the artery wall, distally to the denervation location, in order to stimulate the nerve and trigger an action potential in the nerves surrounding the artery wall, and measure the magnetic field at the proximal location from the denervation position (FIG. 3A), for example using a SQUID magnetometer.

3. Initiate an electric impulse to the artery wall, proximally to the denervation location, in order to stimulate the nerve and trigger an action potential in the nerves surrounding the artery wall, and measure the current density at the distal location from the denervation position, using ultrasound current source density imaging (UCSDI) measurement method, for example as described in FIG. 2.

4. Initiate an electric impulse to the artery wall, distally to the denervation location, in order to stimulate the nerve and trigger an action potential in the nerves surrounding the artery wall, and measure the current density at the proximal location from the denervation position, using ultrasound current source density imaging (UCSDI) measurement method, for example as described in FIG. 2.

5. Initiate an electric impulse to the renal artery wall, proximally to the denervation location, in order to stimulate the nerve and trigger an action potential in the nerves surrounding the artery wall, and measure a change in absolute and/or relative blood pressure, for example using a pressure transducer that is inserted into the artery.

6. Initiate an electric impulse to the renal artery wall distally to the denervation location, in order to stimulate the nerve and trigger an action potential in the nerves surrounding the artery wall, and measure a change in absolute and/or relative blood pressure, for example using a pressure transducer that is inserted into the artery.

7. Initiate an electric impulse to the renal artery wall distally to the denervation location, in order to stimulate the nerve and trigger an action potential in the nerves surrounding the artery wall, and measure the sympathetic neural activity in the brain (FIG. 3B), for example using EEG. Optionally, sympathetic neural activity in the brain is correlated with renal neural activity.

8. Initiate an electric impulse to the renal artery wall distally to the denervation location, in order to stimulate the nerve and trigger an action potential in the nerves surrounding the artery wall, and measure and/or evaluate any visual and/or physical response which is correlated with neural activation.

The described above, for example in sections 6-8, can be performed in other location such as the aorta and/or any other location in which a nerve and/or a nerve bundle was denervated.

In some embodiments, the electric stimulation may be applied using, for example, an intravascular apparatus comprising electrodes, for example an intravascular balloon with electrodes, a catheter, guide wire, guiding catheter, and/or a therapeutic device, for example with integrated electrodes.

In some embodiments, bio impedance measurements of the artery wall are performed, for example following an externally applied stimulation. Optionally, the measurements reflect a change in artery wall tissue condition and/or neural conductivity.

Figure 4:
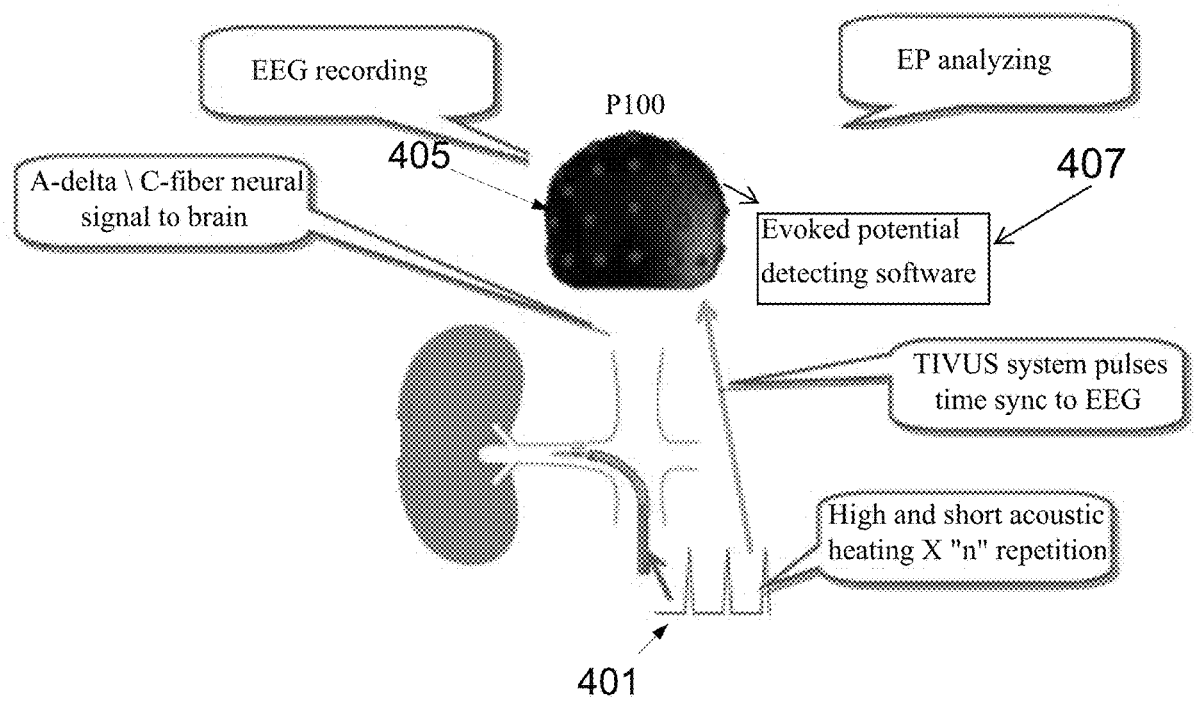
FIG. 4 is a schematic illustration of a method which includes recording evoked potentials before and/or after denervation treatment, according to some embodiments of the invention.

An Exemplary Method for Denervation Assessment which Includes Recording Evoked Potentials Before and/or After a Denervation Treatment FIG. 4 describes a method which includes recording evoked potential before and/or after a denervation treatment, according to some embodiments of the invention.

In some embodiments, the method comprises initiating a short duration pulse of thermal modulation 401 with "n" repetitions distally to the denervation location, in order to stimulate the A-Delta and C-Fiber action potential and measure the activity in the brain by using, for example, evoked potentials measured by EEG 405, EMG, and/or fMRI. In some embodiments, an evoked potential detecting software 407 is used for analysis. In some embodiments, a cooling method may be used instead of thermal modulation.

In some embodiments, the thermal modulation is performed using RF energy, and/or ultrasonic energy. Optionally, the RF energy is unipolar and/or bipolar. Optionally, the ultrasonic energy is emitted as a focused beam. Alternatively, ultrasonic energy is emitted as a non-focused beam. Optionally, the ultrasonic energy is emitted from a single element and/or multiple elements, such as an array of elements.

In some embodiments, a TIVUS™ system is used for emitting ultrasonic energy to achieve thermal modulation. Optionally, the TIVUS™ is connected to a standard EEG recorder and/or to software for detecting evoked potentials.

Figure 5:
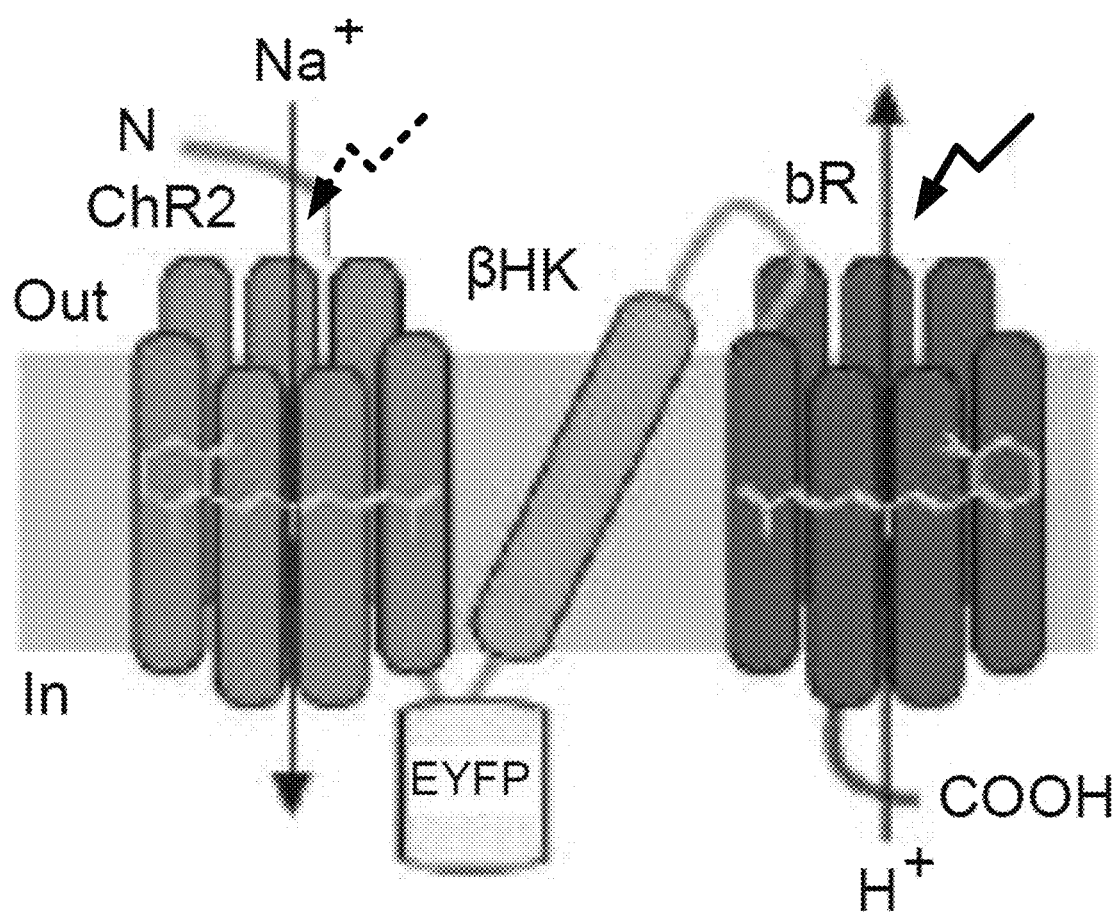
FIG. 5 relates to a method for measuring and/or evaluating renal denervation based on optogenetic controls of neural excitability, according to some embodiments of the invention.

An Exemplary Method for Measuring and/or Evaluating Renal Denervation Based on Optogenetic Controls of Neural Excitability FIG. 5 relates to a method for measuring and/or evaluating renal denervation based on optogenetic controls of neural excitability, according to the expression of light-activated microbial rhodopsins channel rhodospin-2 (ChR2)1 from Chlamydomonas reinhardtii, a cation-permeable channel that enables cell depolarization (neuronal activation) in response to blue light, and halorhodopsin from Natromonas pharaonis (NphR or Halo)2,3, a chloride pump that enables cell hyperpolarization (neuronal silencing) in response to orange light. The ability to drive and block electrical activity at defined locations, for example, at a dendritic spine or a synaptic terminal, may also be beneficial and may require co-localization of ChR2 and NphR.

FIG. 5 shows a design of protein chimeras and functional evaluation of ChR2-EYFP-βbR, ChR2-EYFP-βNphR and hChR2(H134R)-mKate-hβbR. The figure shows a schematic drawing of the ChR2-EYFP-βbR construct after ligation of ChR2-EYFP with βbR. βHK, β helix derived from the H+,K+-ATPase β subunit; bR, bacteriorhodopsin. The dashed arrow indicates blue light spectrum and the continuous arrow indicates orange light spectrum associated with activation of each of the proteins respectively.

In some embodiments, the method comprises exposing the renal artery nerves to blue and/or orange light, proximally to the denervation location, in order to stimulate or suppress neural activity, and measure the change in blood pressure following this action. In some embodiments, an optical fiber and/or LED device are used for delivering light to the renal artery. In some embodiments, the method comprises exposing the renal artery nerves to blue and/or orange light, distally to the denervation location, in order to stimulate or suppress neural activity in nerves surrounding the artery wall, and measure the sympathetic neural activity in the brain.

In some embodiments, the method comprises exposing the renal artery nerves to blue and/or orange light, distally to the denervation location, in order to stimulate or suppress neural activity in nerves surrounding the artery wall, and measure and/or evaluate any visual and/or physical response correlated with neural activation and/or deactivation.

In some embodiments, the method comprises exposing the renal artery nerves to blue and/or orange light, distally to the denervation location, in order to stimulate or suppress neural activity in nerves surrounding the artery wall, and measure absolute and/or relative blood pressure.

An Exemplary General Method for Denervation Treatment and Assessment

Figure 6:
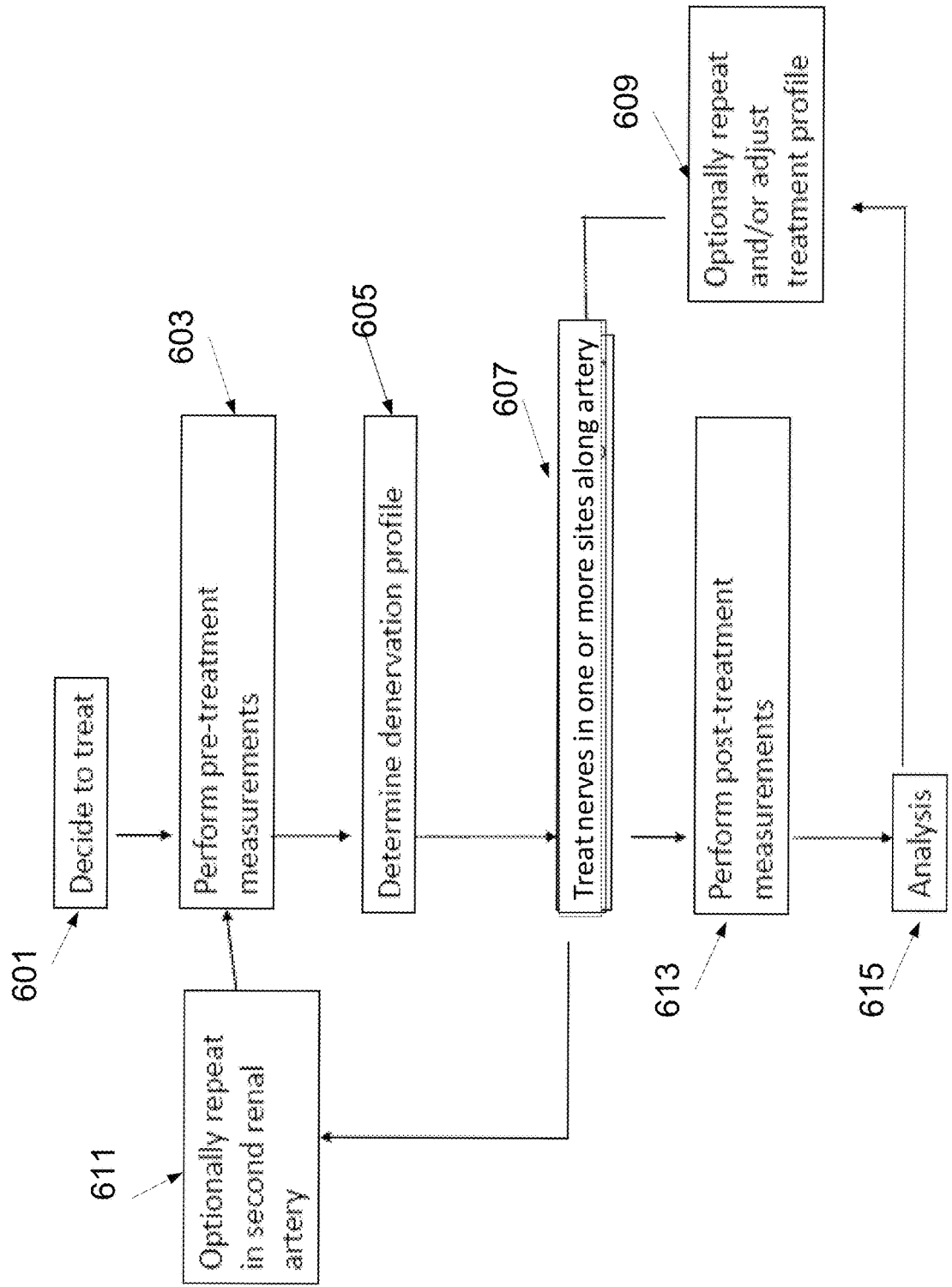
FIG. 6 is a flowchart of a general method for denervation treatment and assessment, according to some embodiments of the invention.

FIG. 6 is a flowchart of a general method for denervation treatment and assessment, according to some embodiments of the invention.

In some embodiments, a decision to perform renal denervation treatment is made, for example by a physician (601). In some embodiments, pre-treatment measurements are performed (603), internally and/or externally to the treated artery. Examples for the pre-treatment measurements include measuring the blood flow rate, blood pressure, and/or a diameter of the renal artery. Optionally, measurements are performed using instruments such as flow wire for example to determine blood flow, a duplex ultrasound device for example to determine a cross section of the artery, and/or a therapeutic device, such as a TIVUS™ device, for example by applying and/or receiving and/or analyzing ultrasonic energy. Optionally, the device is used for performing measurements as well as for applying energy to denervate the nerves.

In some embodiments, a denervation profile is determined (605). Optionally, the profile is determined according to the measured data and/or according to other medical information related to the patient. In some embodiments, determining the denervation profile includes selecting a device for performing the treatment, setting a treatment duration, setting an intensity of the applied energy, etc.

In some embodiments, the treatment is applied at a plurality of locations along the renal artery (607), for example 1 location, 2 locations, 3 locations, 10 locations and/or intermediate or higher numbers of locations. For example, if two locations are selected, one location may be selected adjacent to the main bifurcation, and a second selected at the renal artery ostium. Optionally, the treatment profile is adjusted (609). Optionally, the treatment is repeated for the same renal artery (609), and/or repeated for a second renal artery (611).

In some embodiments, post-treatment measurements are performed (613). Optionally, the post- treatment measurements are performed immediately after the treatment, such as 1 minute, 20 minutes, 1 hour or intermediate time after the treatment. Optionally, the post-treatment measurements are preformed at a later time, such as 1 day, 5 days, 30 days, 60, days, 120 days or intermediate or later times after the treatment. Examples for the post-treatment measurements include measuring the blood flow rate, blood pressure, blood flow velocity, and/or a diameter of the renal artery. Optionally, measurements are performed using a flow wire, a duplex ultrasound device, and/or a therapeutic device, such as a TIVUS™ device.

In some embodiments, measurements are performed during the denervation treatment, for example to determine if the treatment profile needs to be adjusted and/or if the treatment duration should be lengthened.

In some embodiments, pre and/or post treatment measurements are performed distally to the denervation site, for example at a distance ranging between 5-10 cm from the denervation location. Additionally and/or alternatively, measurements are performed proximally to the denervation site, for example at a distance ranging between 0.1-5 cm from the denervation location, for example in vertical and/or horizontal directions in the artery.

In some embodiments, the measured data is analyzed (615). Optionally, post-treatment measurements are compared to the pre-treatment measurements. In one example, the renal blood flow rate is analyzed. Optionally, a threshold is determined in order to decide if the treatment should be repeated. For example, if the renal blood flow rate measured post-treatment, for example immediately post treatment, is not at least 100%, 50%, 70%, 150%, and/or higher, smaller or intermediate percentages higher than the blood flow rate measured pre-treatment, the denervation treatment is repeated. Optionally, the blood flow rate changes over time, and a threshold may be predefined accordingly if the blood flow rate measurement is repeated, for example, 2 days, 1 month, months, or any other time after the denervation treatment.

Figure 7:
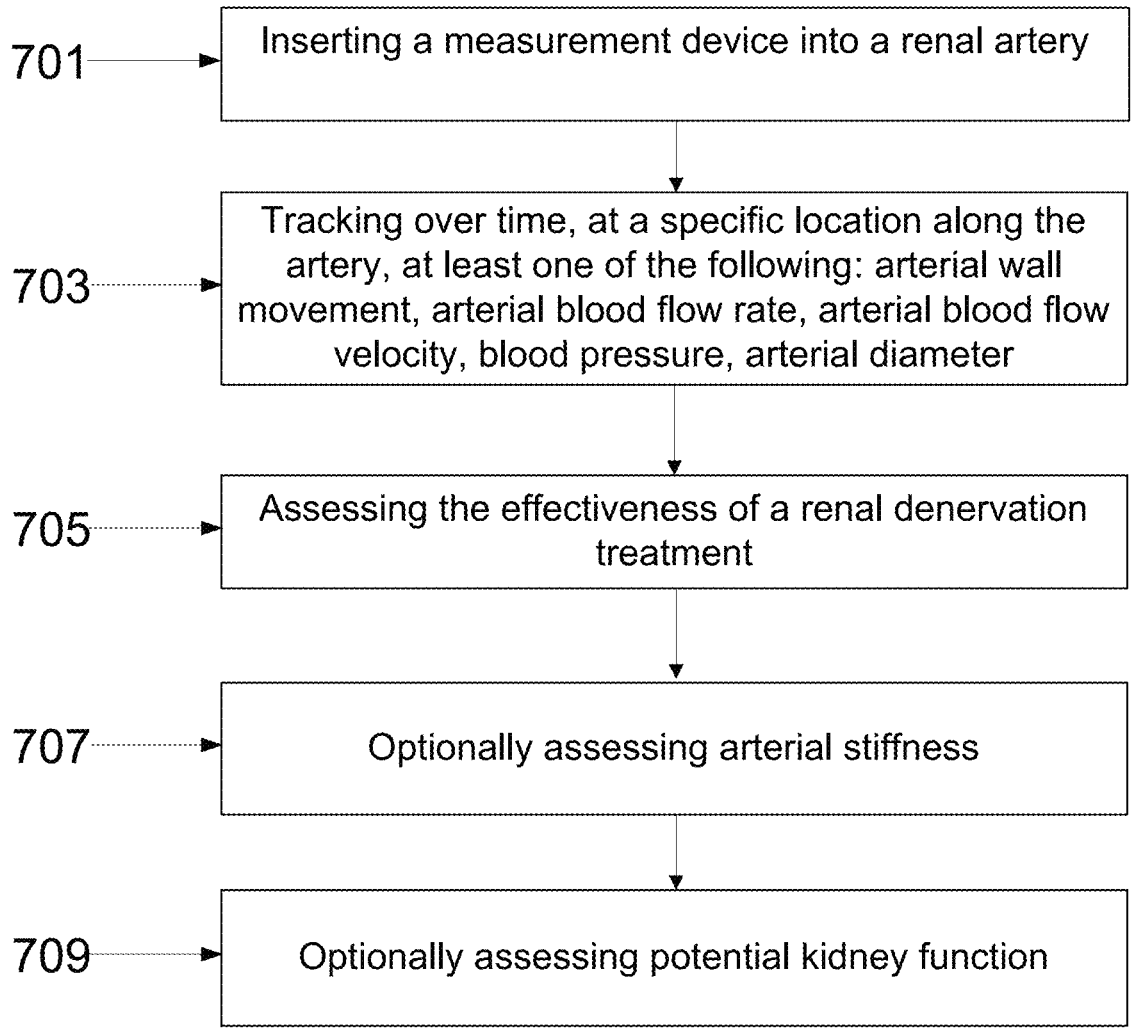
FIG. 7 is a flowchart of a method for assessing denervation treatment by tracking physiological changes at a specific location in the artery over time, according to some embodiments of the invention.

An Exemplary Method for Assessing Denervation Treatment by Tracking Physiological Changes at a Specific Location Along the Artery Over Time FIG. 7 is a flowchart of a method for assessing denervation treatment by tracking physiological changes at a specific location along the artery over time, according to some embodiments of the invention.

In some embodiments, a measurement device is inserted into a renal artery (701). Optionally, the measurement device is mounted on a catheter tip. In some embodiments, the measurement device comprises an ultrasonic transceiver and/or transducer, for example a TIVUS™ device, which is adapted for applying ultrasonic energy for example to cause tissue ablation to denervate nerves, and/or adapted for receiving ultrasonic energy such as returning echo signals from walls of an artery. In some embodiments, measurements are performed externally to the artery, for example using a duplex ultrasound device. Other examples of measurement devices and/or systems may include a flow wire, a duplex ultrasound catheter, a CT angiography system, an MRI angiography system and/or any other device capable of measuring at least one of the parameters described herein.

In some embodiments, using the measurement device, one or more of the following parameters are tracked over time: arterial wall movement, arterial blood flow rate, arterial blood flow velocity, blood pressure, and/or arterial diameter (703).

In some embodiments, measurements are performed at a specific location along the artery, for example at a nerve denervation location. Optionally, measurements are performed at a non-treated location, for example a location found in some distance from a nerve denervation location, such as 0.1 cm, 2 cm, 5 cm or smaller, intermediate, or larger distances from a denervation location.

In some embodiments, tracking over time comprises measuring the above mentioned parameters before and/or during and/or after a denervation treatment. In one example, blood flow rate and/or blood pressure are measured continuously throughout the treatment procedure, for example tracked for 2-5 hours continuously. In some embodiments, measurements are performed periodically, for example every 1 second, every 30 seconds, every minute, every 5 minutes, every 1 hour, or any other time intervals. Optionally, a measurement is performed only once.

In some embodiments, by analyzing the measurement results, the effectiveness of the denervation treatment is assessed (705). In some embodiments, analyzing comprises comparing measurements taken before and/or during and/or after a denervation treatment, for example changes to arterial diameter may be analyzed to detect a widening or a narrowing of the artery at one or more locations along the artery. In some embodiments, analyzing comprises combining two or more measured parameters, such as the blood flow rate and the arterial diameter at a specific location, to determine the effectiveness of the treatment. Optionally, combining results may point to a possible synergy between two or more parameters. Optionally, combining results may reduce systemic errors.

In some embodiments, analyzing comprises detecting a maximal and/or minimal diameter of the artery, and/or detecting a pattern in arterial wall movement over time.

In some embodiments, arterial wall movement is determined by measuring a distance between an arterial wall and a catheter that is inserted into the renal artery, such as a TIVUS catheter. Optionally, distance is measured using ultrasonic imaging. Optionally, an additional element is used in order to affix the measurement device in position during distance measurement, for example to maintain a catheter in the center of the artery with respect to the artery walls.

In some embodiments, arterial wall movement is determined using a two dimensional ultrasonic device, for example externally to the artery. In some embodiments, arterial wall movement and/or arterial diameter are detected and measured by ultrasonic imaging. In some embodiments, arterial wall movement is measured, and the arterial diameter is deduced from the wall movement measurement.

Some embodiments comprise assessing arterial stiffness (707), for example by tracking arterial wall movement over time. Optionally, the differences in amplitudes of the arterial wall movement due to pulsation indicate the capability of the artery to expand. A low expansion ability of the artery may indicate a high level of arterial stiffness, and vice versa.

Some embodiments comprise assessing potential kidney function (709), for example to determine the extent of blood pressure regulation and decide whether sufficient treatment was performed to prevent hypertension. In some embodiments, kidney function assessment is determined according to the level of arterial stiffness. For example, a high level of arterial stiffness may be linked to high blood pressure, whereas blood pressure is at least partially regulated by the kidney.

In some embodiments, the results of the measurements directly indicate a condition of the renal nerves. In some embodiments, the results of the measurements indicate the functioning of the kidney. In some embodiments, blood flow measurements such as blood flow rate and/or velocity measurements are correlated with kidney function.

In some embodiments, a blood pressure regulating medication is given to a patient. Optionally, measurements of physiological changes are performed following an effect induced by the medication.

An Exemplary Detailed Method for Evaluating Mechanical Parameters of the Artery for Assessing Renal Denervation In some embodiments, the method includes performing baseline measurements, for example before the treatment, such as 1 day, 2 hours, 30 minutes, 5 minutes or any other times before the treatment. Optionally, if the measurement is performed immediately before the treatment, stress experienced by the patient may affect the measurement results. Optionally, two or more baseline measurements are performed, for example one measurement a week before the treatment, and a second measurement immediately before the treatment, to provide a more accurate estimation.

Figure 8:
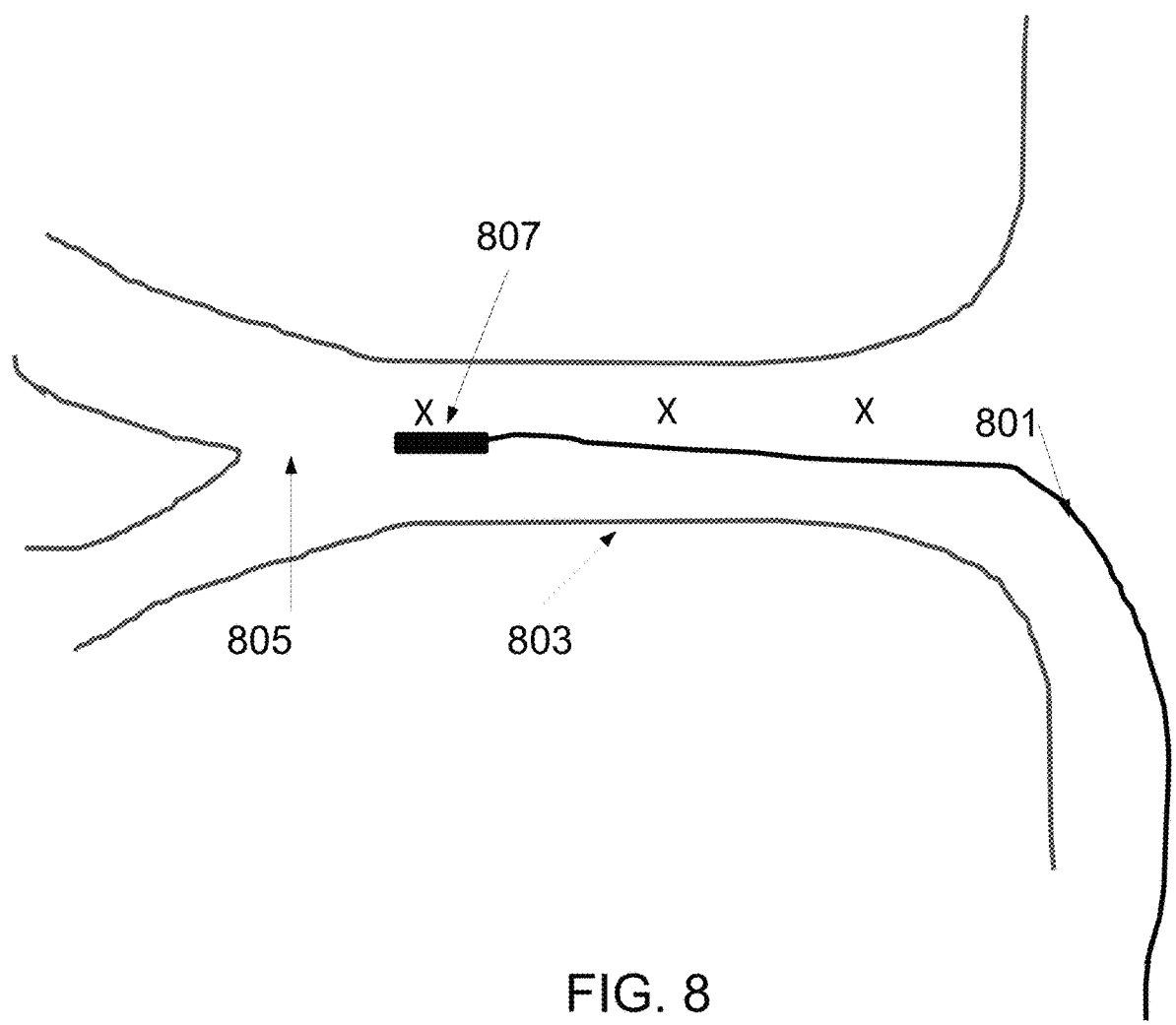
FIG. 8 is a drawing of a flow wire inserted into a renal artery, according to an exemplary method for evaluating mechanical parameters of the artery for assessing renal denervation.
Figure 9:
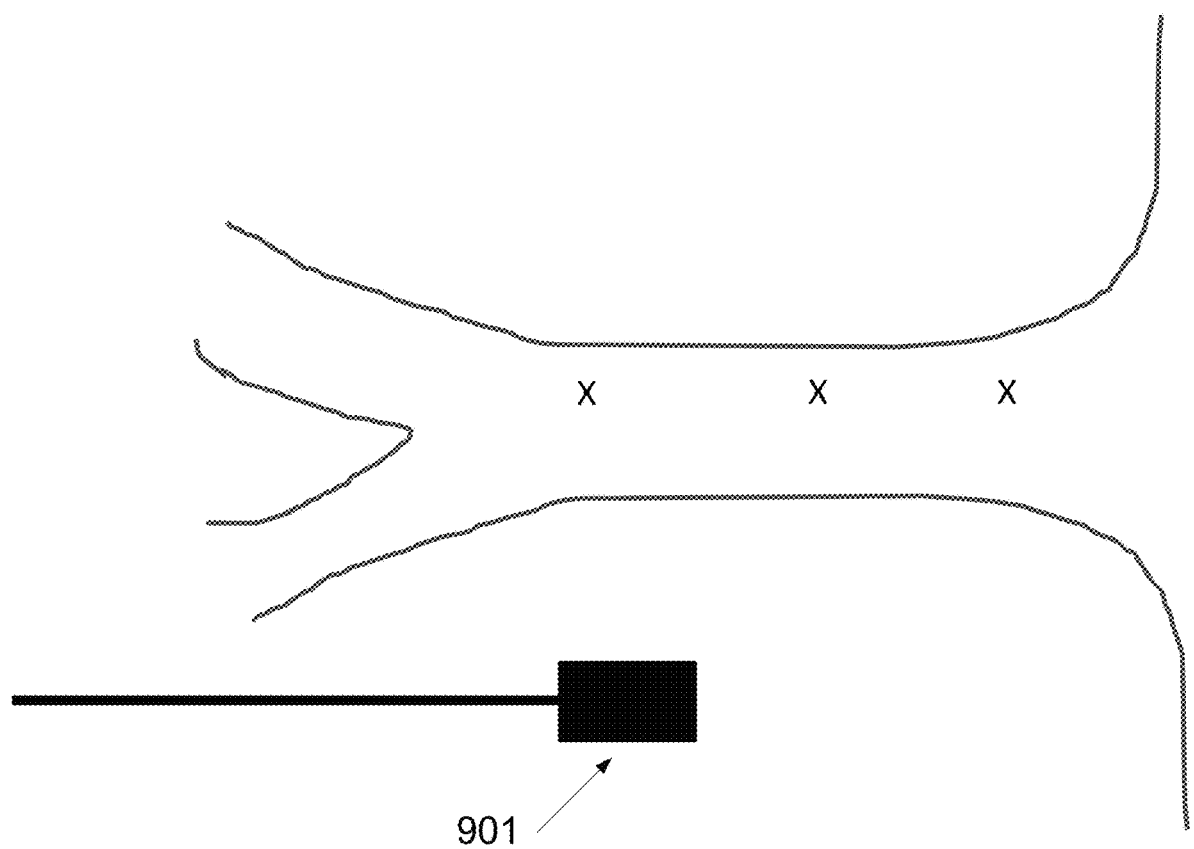
FIG. 9 is a drawing of a duplex ultrasound device positioned externally to a renal artery, according to an exemplary method for evaluating mechanical parameters of the artery for assessing renal denervation.

In some embodiments, the measurements include measuring a diameter of the artery, measuring renal blood flow rate, measuring renal blood flow velocity, measuring blood pressure and/or measuring artery wall movement. In some embodiments, measurements are performed from within a lumen of the artery. Additionally and/or alternatively, measurements are performed externally to the artery. Optionally, as shown, for example, in FIG. 8, a flow wire 801 or any other flow measurement device can be inserted into the renal artery, for example via a femoral approach, to measure flow rate and/or velocity. Optionally, the flow wire can be positioned at a distal segment of the main stem of the renal artery 803, for example in proximity to the main bifurcation 805, or at any other location along the artery. Optionally, measurements are performed at one or more locations 807 along the artery (marked by X's). Optionally, an external duplex ultrasound device 901, as shown for example in FIG. 9, can be used, for example, to determine a diameter of the artery. In some embodiments, a TIVUS™ catheter is used for measuring one or more of the parameters described herein, for example comprising ultrasonic transceivers to measure arterial diameter by measuring a distance to an artery wall, according to returning echo signals from the artery walls.

In some embodiments, the method includes inserting a device for performing renal denervation into a renal artery, for example a TIVUS™ catheter, or any other renal denervation system. Optionally, energy such as RF and/or ultrasonic energy is applied to cause tissue ablation and denervate nerves along and/or within the artery, for example nerves surrounding the main stem of the renal artery. In some embodiments, treatment is applied to several selected locations, for example 3, 5, 10 or intermediate, higher, or small number of locations. In some embodiments, ultrasonic energy is applied in one or more directions, such as 1,2,3,4,5,6 directions, for example circumferentially towards the artery walls. In some embodiments, a duration of treatment at each of the locations ranges, for example, between 10-200 seconds. In some embodiments, various frequencies and intensities may be applied, for example a frequency of 10 MHz and an intensity of 30-40 W/cm^2 may be used.

In some embodiments, the method includes performing post denervation measurements, for example 5 minutes, 20 minutes, 30 minutes, 1 day, 2 days after the treatment. In some embodiments, measurements are performed in the same location that they were performed before the treatment and/or during the treatment. In some embodiments, measurements are performed immediately after the treatment is completed and/or immediately after denervation at each of the locations along the artery. Optionally, a TIVUS catheter is used for performing the measurements. Alternatively, the TIVUS catheter is removed before measuring, for example measuring blood flow rate, so as to not interrupt the blood flow through the artery.

In some embodiments, the pre-denervation measurements and the post-denervation measurement and/or measurements performed during the treatment are compared in order to determine the effectiveness of the renal denervation treatment.

VARIOUS EMBODIMENTS OF THE INVENTION

Some embodiments of the invention relate to measuring neural activity, conductivity and/or continuity before and/or during and/or after a denervation treatment, for example to determine the effectiveness of the treatment.

In some embodiments, measurements are conducted in real time and/or for example immediately after the procedure, optionally reducing and/or eliminating the need for chemical based measurements which may reflect denervation after a relatively long period of time, such as days or months, depending on the chemical marker that was used.

Some embodiments of the invention relate to measuring renal neural activity. Some embodiments comprise estimating neural activity in other organs of the body using the methods described herein. Optionally, various physiological responses are determined using the methods described herein.

Some embodiments of the methods and/or apparatuses may include a standalone and/or integrated system comprising:
- a console that controls parts of the system used for applying treatment and/or for measuring and/or for initiating stimulation. Optionally, the console performs analysis and/or contains a user interface and/or displays measurements and/or communicates with additional devices and/or initiates triggering, such as neural stimulation.
- one or more parts for applying measurements and/or initiating triggering and/or treating, such as electrodes, transceivers, and/or transducers.
- an integrated device and/or software that is a part of an existing or commonly used measurement and/or imaging systems and/or triggering systems.

Some embodiments of the methods and/or apparatuses of the components used for applying treatment and/or for stimulating and/or for measuring may be mounted on and/or assembled to:
- a guide wire
- a guiding catheter
- a standalone catheter with a sensing head and/or body
- one or more sensors that are integrated onto an existing device The described methods can be performed, for example, prior to and/or post denervation treatments in order to compare relative neural activity prior to and post denervation; and to detect an absolute value of neural activity which may reflect neural conductivity and/or continuity.

Some embodiments include implementing a signal processing analysis, for example to achieve a higher signal to noise ratio and/or reflect trends and/or special phenomenon. The analysis may include, for example, a smoothing algorithm, FFT, a pattern matching algorithms, etc. For example, FFT may be applied to returning echo signals received by ultrasonic transceivers, for example of the TIVUS device, to determine, for example, wall movement as a function of time. In another example, FFT may be applied to EEG signals that are recorded in the brain during stimulation of the renal artery nerves.

In some embodiments, methods for verifying and/or validation renal denervation treatment are based on the following:

Sympathetic neural control affects not only small resistance arteries but also the mechanical properties of large arteries. For example, pharmacological or electrical activation of the sympathetic nervous system has been shown to reduce distensibility of small and medium-size arteries in animals. Furthermore, maneuvers that increase sympathetic stimulation have been associated with a reduction of radial artery distensibility in humans. Furthermore, there is evidence that in animals, small-artery distensibility is increased by the removal of sympathetic influences and that in humans, radial artery distensibility increases after transient anesthesia of the brachial plexus. This suggests that the sympathetic nervous system may increase arterial wall stiffness not only physically but also tonically. In addition, there is growing evidence that both sympathetic over activity and arterial stiffening are implicated in the development of hypertension and its complications. Sympathetic activity may contribute to myocardial hypertrophy and vascular remodeling. Experimental studies suggest that sympathetic neural mechanisms may have a stiffening influence on arterial mechanical properties. In rats, sympathectomy and a receptor blockade increase distensibility of both carotid and femoral arteries. These suggest that sympathetic vasoconstrictor mechanisms modulate arterial elastic properties. Indeed, in humans, removal of adrenergic tone by anesthesia of the brachial plexus and the spinal cord results in marked increased distensibility of radial artery and femoral artery, respectively.

Optionally, based on the above, some embodiments include the following methods and/or combinations of them, for example to determine the effectiveness of a renal denervation treatment.

Some embodiments comprise measuring renal artery stiffness using ultrasonic imaging techniques.

Some embodiments comprise measuring renal artery wall movement using ultrasonic echo measurement from artery wall.

Some embodiments comprise measuring renal artery wall movement's amplitude in a given duration using ultrasonic echo measurement from artery wall. Optionally, the amplitude is measured with respect, but not limited to, blood pressure and/or pulsation.

Some embodiments comprise measuring a diameter of the renal artery using ultrasonic imaging techniques. Optionally, the diameter is measured with respect, but not limited to, blood pressure and/or pulsation.

Some embodiments comprise measuring renal artery stiffness using Pulse Wave Velocity measurement method, for example by using pressures sensors distally and/or proximally to the denervation location inside the renal artery.

Some embodiments comprise measuring absolute blood flow and/or a change in blood flow prior to and/or post denervation. Optionally, a change is blood flow rate reflects neural activity level and/or a condition of the nerves. In some embodiments, the blood flow measurement can be combined with one or more of the following: initiation of an electric impulse to the artery wall, proximally to the denervation location, and/or an injection of a drug to the kidney, to regulate blood pressure.

In some embodiments, any of the above parameters such as blood flow rate, artery diameter, and/or artery wall movement are measured before and/or after the denervation procedure. In some embodiments, the measured values are compared. Optionally, the measured values are analyzed using a signal processing method.

In some embodiments, any of the above parameters are compared to previously known values, for example pre-research values.

In some embodiments, a formula and/or table is used for analyzing the measured data.

Following is a list of methods/and or features and/or devices and/or systems relating to the assessment of renal denervation effectiveness, according to some embodiments of the invention:

A. Some embodiments relate to a medical measurement device for sensing the neural activity comprising at least one magnetometer that is positioned inside a vessel.

B. Some embodiments relate to a device, for example a device according to section A, wherein the magnetometer is a SQUID magnetometer.

C. Some embodiments relate to a device, for example a device according to section B, wherein the SQUID magnetometer comprises at least one coil.

D. Some embodiments relate to a medical measurement device for imaging neural activity, which comprises at least one of the following:
  High spatial resolution ultrasonic imaging
  Ultrasound current source density imaging (UCSDI)
  Acoustoelectric (AE) modulated voltage recordings to map and reconstruct current densities E. Some embodiments relate to a medical measurement device for sensing neural activity, which comprises at least one bio impedance measurement sensor.

F. Some embodiments relate to a medical measurement system for measuring at least one mechanical parameter of a blood vessel together with at least one of the following manipulations, in order to estimate renal denervation:
  Electric impulse to the artery wall, proximally to the denervation location
  Injection of a drug to the kidney to regulate blood pressure G. Some embodiments relate to a system, for example a system according to section F, wherein the system controls and synchronizes the manipulations and measuring techniques.

H. Some embodiments relate to a device, for example a device according to section A and section D, wherein the device is included in a system which further comprises at least one of the following:
  A stimulator to the artery wall that stimulates the nerves
  Means for synchronizing between the stimulator and the measurement device I. Some embodiments relate to a system, for example the system according to section H, wherein the stimulator is an electric impulse stimulator.

J. Some embodiments relate to a system, for example the system according to sections H, and I, wherein synchronization is based on stimulating nerves distally to the treated location, and measuring proximally to the treated location.

K. Some embodiments relate to a system, for example the system according to sections H, and I, wherein synchronization is based on stimulating nerves proximally to the treated location and measuring distally to the treated location.

L. Some embodiments relate to a system, for example the system according to section F, wherein the mechanical parameter is blood flow.

M. Some embodiments relate to a system, for example the system according to section F, wherein the mechanical parameter is blood pressure.

N. Some embodiments relate to a device that electrically stimulates the artery wall by causing evoked potential in the nerves surrounding the artery.

O. Some embodiments relate to a device, for example a device according to section N, wherein the device is included in a system that further comprises at least one of the following features:
  Measuring the sympathetic activity in the brain
  Measuring and/or evaluating any visual and/or physical responses which are correlated with neural activation.
  Measuring EEG in a specific location
  Measuring fMRI
  Synchronizing between the stimulator and the measurement device P. Some embodiments relate to a device that thermally heats the artery wall for causing evoked potential in C-fibers and A-delta nerves surrounding the artery.

Q. Some embodiments relate to a device, for example a device according to section P, which is combined in a system comprising at least one of the following:
  Measuring the sympathetic activity in the brain
  Measuring and/or evaluating any visual and/or physical responses which are correlated with neural activation.
  Measuring EEG in a specific location
  Measuring fMRI
  Synchronizing between the stimulator and the measurement device R. Some embodiments relate to a device that stimulates the nerves surrounding the artery by exposing the nerve to at least one of the following:
  Blue light
  Orange light S. Some embodiments relate to a device, for example the device according to section R, wherein the device is included in a system which further comprises at least one of the following features:
  Measuring the sympathetic activity in the brain
  Measuring and/or evaluating any visual and/or physical responses which are correlated with neural activation.
  Measuring EEG in a specific location
  Measuring fMRI T. Some embodiments relate to a device, for example the device according to section N, wherein the electric stimulator is at least one of the following:
  Intravascular Balloon with electrodes
  Intravascular apparatus includes electrodes
  Catheter and/or guide wire and/or guiding catheter and/or a therapeutic device with integrated electrodes.

U. Some embodiments relate to a medical measurement device for evaluating renal denervation comprising at least of the following features:
  Measuring renal artery stiffness using ultrasonic imaging techniques Measuring renal artery wall movement using ultrasonic echo measurement from artery wall Measuring renal artery wall movement amplitude in a given duration using ultrasonic echo for measuring the distance between the sensing element and the artery wall, with respect, but not limited, to blood pressure Measuring renal artery diameter using ultrasonic imaging techniques, with respect, but not limited, to blood pressure Measuring renal artery stiffness using Pulse Wave Velocity (PWV) measurement method, by using pressure sensors distally and/or proximally to denervation location inside the renal artery.

V. Some embodiments relate to a device, for example according to any of the sections herein, wherein the imaging is performed distally to the denervation location.

W. Some embodiments relate to a device, for example according to any of the sections herein, wherein the imaging is performed proximally to the denervation location.

X. Some embodiments relate to a device, for example according to any of the sections herein, wherein imaging and/or measuring is performed prior to the renal denervation procedure.

Y. Some embodiments relate to a device, for example according to any of the sections herein, wherein imaging and/or measuring is performed after a renal denervation procedure.

Z. Some embodiments relate to a device, for example according to any of the sections herein, wherein imaging and/or measurement results are compared to pre-research results.

Aa. Some embodiments relate to a device, for example according to any of the sections herein, wherein imaging and/or measurement results are compared to a table and/or formula that evaluates denervation rate.

Bb. Some embodiments relate to a device, for example according to any of the sections herein, wherein the sensing and/or measuring method is actuated and/or applied by and/or combined to one of the following:

An intravascular Balloon
An intravascular apparatus
A catheter
A guide wire
A therapeutic device
A sheath In some embodiments, devices and/or systems and/or methods and/or components as described in one or more of the following applications may be used for measuring renal denervation effectiveness using methods described herein:

PCT/IB2011/054634 filed on Oct. 18, 2011, entitled "THERAPEUTICS RESERVOIR", relating to a method of drug delivery and, more particularly, to a method for trapping drugs to form a drug reservoir in tissue;

PCT/IB2011/054635 filed on Oct. 18, 2011, entitled "ULTRASOUND EMISSION ELEMENT", showing, for example, an apparatus for generating relatively high efficiency ultrasound;

PCT/IB2011/054636 filed on Oct. 18, 2011, entitled "AN ULTRASOUND TRANSCEIVER AND USES THEREOF", showing for example, a method for feedback and control of the ultrasonic transducer;

PCT/IB2011/054641 filed on Oct. 18, 2011, entitled "AN ULTRASOUND TRANSCEIVER AND COOLING THEREOF", showing for example, a method for blood flow cooling of the ultrasonic transducer;

"PCT/IB2011/054640 filed on Oct. 18, 2011, entitled "TISSUE TREATMENT", showing for example, a method of selective targeting and treating tissues using ultrasound; For example, this application teaches: "In an exemplary embodiment of the invention, beam 1228 is unfocused, for example, beam does not converged at a point, for example, beam diverges relatively little. In an exemplary embodiment of the invention, the shape of element 102 is rectangular. Optionally, element 102 is planar. Optionally, a length of element 102 is, for example, about 1 mm, about 2 mm, about 4 mm, about 6 mm, about 8 mm, about 10 mm, or other smaller, intermediate or larger lengths are used. Optionally, a width of element 102 is, for example, about 0.2 mm, about 0.6 mm, about 1.0 mm, about 1.4 mm, about 2.0 mm, or other smaller, intermediate or larger widths are used. In an exemplary embodiment of the invention, beam 1228 produced by a rectangular acoustic element is relatively straight, spreading an angle of about fifteen degrees relative to the exposed surface of element 102, when measured along the length." (page 32 starting on line 9); in another example, this application teaches: "The therapeutic treatment on the blood vessel wall is done with no mechanical contact with the vessel wall, thereby reducing or eliminating the danger of damaging the vessel wall or disrupting any pathologies on the wall (e.g., atherosclerotic plaques). For example, reducing the risk of arterial perforation and/or mechanical damage that might cause a narrowing in the vessel, plaque tear and/or emboli." (page 67 starting on line 17); in another example, this application teaches "Estimated or measured flow rate of blood across the surface of the acoustic element is important for controlling the temperature of the element to prevent overheating. In some embodiments, the flow rate of the blood is adjusted relatively higher or relatively lower, such as to control the temperature. Estimated or measured flow rate of blood across the wall of the treatment target (e.g., blood vessel) is important for estimating the cooling capacity of the blood on the tissues of the wall being heated by ultrasound." (page 20 starting on line 1); in another example, this application teaches "A particular feature of some embodiments of the invention is that an extent of treatment in a dimension perpendicular to the lumen wall is affected both by cooling of the lumen wall, e.g., by natural blood flow and by dissipation of energy as the energy penetrates into the tissue." (page 16 starting on line 13)."

PCT/IB2011/054638 filed on Oct. 18, 2011, entitled "SEPARATION DEVICE FOR ULTRASOUND ELEMENT", showing for example, a device to prevent the transducer from touching the blood vessel wall; and PCT/IB2011/054639 filed on Oct. 18, 2011, entitled "AN ULTRASOUND TRANSCEIVER AND CONTROL OF A THERMAL DAMAGE PROCESS", showing for example, an ultrasound transceiver and to control of an ablation or thermal damage process to a tissue.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It is the intent of the applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

The following is a list of references which may be relevant to the methods and/or apparatuses and/or features disclosed herein:

REFERENCES

[1] Magnetic Field of a Nerve Impulse: First Measurements John P. Wikswo, John P. Barach, John A. Freeman Science, Vol 208 (4439), pp 53-55, 1980

[2] A gene-fusion strategy for stoichiometric and co-localized expression of light-gated membrane proteins Sonja Kleinlogel1, Ulrich Terpitzl,4, Barbara Legruml, Deniz Gökbugetl,4, Edward S Boyden2, Christian Bamannl, Phillip G Woodl & Ernst Bambergl,3

[3] Ultrasound Current Source Density Imaging Ragnar Olafsson, Student Member, IEEE, Russell S. Witte, Member, IEEE, Sheng-Wen Huang, Member, IEEE, and Matthew O'Donnell, Fellow, IEEE

[4] Effect of Sympathectomy on Mechanical Properties of Common Carotid and Femoral Arteries Arduino A. Mangoni; Luca Mircoli; Cristina Giannattasio; Giuseppe Mancia; Alberto U. Ferrari

[5] An independent relationship between muscle sympathetic nerve activity and pulse wave velocity in normal humans Ewa S'wierblewskaa, Dagmara Heringa, Tomas Karab, Katarzyna Kunickaa,Piotr Kruszewskia, Leszek Bieniaszewskia, Pierre Boutouyriec, Virend K. Somersb and Krzysztof Narkiewicza,b

What is claimed is:

1. A system for determining effectiveness of a renal denervation treatment, the device comprising:
   an elongate catheter;
   one or more ultrasonic transceivers functionally comprised in the elongate catheter adapted for emitting ultrasound energy suitable for nerve denervation and for receiving non-imaging ultrasound signals, said non-imaging ultrasound signals comprise echo signals reflected by a renal artery wall; and
   a processor adapted to determine renal artery stiffness based on processing received ultrasound signals, wherein said system is configured to use a single ultrasonic transceiver of said one or more ultrasonic transceivers and which is adapted for both emitting ultrasound energy suitable for nerve denervation and for receiving ultrasound signals processing by the processor.

2. The system according to claim 1, configured to determine effectiveness of the renal denervation treatment continuously during the denervation treatment.

3. The system according to claim 1, wherein the processor is adapted to determine renal artery diameter using the ultrasonic transceiver to receive ultrasound echo signals reflected by a renal artery wall.

4. The system according to claim 1, wherein the processor is adapted to determine effectiveness by analyzing measurement results of both arterial wall movement and arterial diameter.

5. The system according to claim 1, configured to measure arterial wall movement and arterial diameter at least 5 times, periodically every 30 seconds.

6. The system according to claim 1, wherein the processor is adapted to determine renal artery stiffness based on measuring renal artery wall movement using the ultrasonic transceiver to receive ultrasound echo signals reflected by a renal artery wall.

7. The system according to claim 6, wherein the processor is adapted to calculate an amplitude of the artery wall movement by measuring a distance between at least one of said transceivers and the artery wall.

8. The system according to claim 1, wherein the processor is adapted to measure a diameter of the renal artery using ultrasonic imaging.

9. The system according to claim 1, wherein the processor is adapted to measure renal artery stiffness by calculating pulse wave velocity.

10. The system according to claim 1, wherein the processor is adapted to measure a distance between the at least one transceiver and the renal artery wall.

11. The system according to claim 10, wherein the processor is adapted to assess arterial wall movement based on measuring distance between the at least one transceiver and the renal artery wall.

12. The system according to claim 10, wherein the processor is adapted to analyze results of measuring distance between the at least one transceiver and the renal artery wall by applying Fast Fourier Transform to reflected echo signals to determine artery wall movement as a function of time.

13. The system according to claim 1, configured to transmit non-focused ultrasound.

14. The system according to claim 1, wherein the catheter and the ultrasonic transceiver are sized to fit within a renal artery.

15. The system according to claim 1, wherein the transceiver is rectangular.

16. The system according to claim 1, wherein the processor is adapted to determine if a denervation treatment should be repeated by applying a threshold to at least one of arterial wall movement and arterial diameter.

17. The system according to claim 1, wherein the processor is adapted to adjust a denervation treatment profile according to results of determination of the renal artery stiffness.

18. The system according to claim 1, wherein the processor is adapted to determine effectiveness by comparing pre-denervation and post-denervation measurements.

19. The system according to claim 1, comprising at least one nerve activity sensor which generates a nerve activity signal; and wherein said processor is adapted to determine treatment effect on nerves based on a signal from said nerve activity sensor.

20. The system according to claim 19, comprising a nerve stimulator and wherein said processor detects said stiffness and/or said nerve activity in response to stimulation by said stimulator.

21. The system according to claim 19, wherein said nerve activity sensor comprises ultrasonic transmission.

22. The system according to claim 1, wherein both the emitted ultrasound energy and the received ultrasound signals are unfocused.

23. A system for determining effectiveness of a renal denervation treatment, the device comprising:
  an elongate catheter;
  at least one ultrasonic transceiver functionally comprised in the elongate catheter adapted for emitting ultrasound energy suitable for nerve denervation and for receiving ultrasound signals;
  at least one electrical nerve stimulator; and
  a processor adapted to determine (a) renal artery stiffness based on processing received ultrasound signals and (b) treatment effectiveness based on a measured response of a renal wall or a nerve to stimulation by said nerve stimulator.

24. A system for determining effectiveness of a renal denervation treatment, the device comprising:
  an elongate catheter;
  at least one ultrasonic transceiver functionally comprised in the elongate catheter adapted for emitting unfocused ultrasound energy suitable for nerve denervation and for receiving ultrasound signals; and
  a processor adapted to determine renal artery stiffness based on processing received non-imaging ultrasound signals used for measurement; said non-imaging ultrasound signals comprise echo signals reflected by a renal artery wall.

* * * * *